(12) United States Patent
Melcher et al.

(10) Patent No.: US 11,900,437 B2
(45) Date of Patent: *Feb. 13, 2024

(54) DATA MESH BASED ENVIRONMENTAL AUGMENTATION

(71) Applicant: eBay Inc., San Jose, CA (US)

(72) Inventors: Ryan Melcher, Ben Lomond, CA (US); John Tapley, San Jose, CA (US); Robert Lee, Burlingame, CA (US)

(73) Assignee: EBAY INC., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/134,815

(22) Filed: Apr. 14, 2023

(65) Prior Publication Data

US 2023/0298082 A1 Sep. 21, 2023

Related U.S. Application Data

(63) Continuation of application No. 17/538,491, filed on Nov. 30, 2021, now Pat. No. 11,657,443, which is a
(Continued)

(51) Int. Cl.
*H04L 29/06* (2006.01)
*G06Q 30/0601* (2023.01)
(Continued)

(52) U.S. Cl.
CPC ........... *G06Q 30/0631* (2013.01); *A61B 5/24* (2021.01); *G06Q 30/0633* (2013.01);
(Continued)

(58) Field of Classification Search
CPC .. G06Q 30/0631; G06Q 30/0633; A61B 5/24; G06T 11/206; H04L 43/04;
(Continued)

(56) References Cited

U.S. PATENT DOCUMENTS 5,794,178 A 8/1998 Caid et al.
6,014,661 A 1/2000 Ahlberg et al.
(Continued)

FOREIGN PATENT DOCUMENTS

CN 106462825 A 2/2017
CN 115496556 A 12/2022
(Continued)

OTHER PUBLICATIONS

U.S. Appl. No. 14/498,326 U.S. Pat. No. 9,576,312, filed Sep. 26, 2014, Data Mesh-Based Wearable Device Ancillary Activity.
(Continued)

*Primary Examiner* — Harunur Rashid
(74) *Attorney, Agent, or Firm* — SCHWEGMAN LUNDBERG & WOESSNER, P.A.

(57) ABSTRACT

In various example embodiments, a system and method for data mesh-based environmental augmentation are presented. Attribute data associated with a user may be received from a plurality of attribute sources. A portion of the attribute data may include real-time data. A portion of the real-time data indicative of an identity of the user may be identified. The identity of the user may be authenticated with respect to the real-time data by analyzing the identified portion of the real-time data. Based on the authentication of the identity of the user, a user activity being performed by the user may be identified based on the real-time data, and the user activity may be augmented according to a user setting.

17 Claims, 18 Drawing Sheets

Related U.S. Application Data continuation of application No. 16/391,852, filed on Apr. 23, 2019, now Pat. No. 11,210,723, which is a continuation of application No. 14/449,126, filed on Jul. 31, 2014, now Pat. No. 10,304,114.

(60) Provisional application No. 61/970,263, filed on Mar. 25, 2014.

(51) Int. Cl.

| | |
|---|---|
| A61B 5/24 | (2021.01) |
| G06T 11/20 | (2006.01) |
| H04L 43/04 | (2022.01) |
| H04L 67/10 | (2022.01) |
| H04L 9/40 | (2022.01) |
| H04W 76/14 | (2018.01) |
| H04W 4/80 | (2018.01) |
| H04L 67/1042 | (2022.01) |
| H04W 84/18 | (2009.01) |
| H04L 101/69 | (2022.01) |

(52) U.S. Cl.
CPC .......... *G06T 11/206* (2013.01); *H04L 43/04* (2013.01); *H04L 63/08* (2013.01); *H04L 63/107* (2013.01); *H04L 67/10* (2013.01); *H04L 67/1042* (2013.01); *H04W 4/80* (2018.02); *H04W 76/14* (2018.02); *H04W 84/18* (2013.01); *H04L 2101/69* (2022.05)

(58) Field of Classification Search
CPC ....... H04L 63/08; H04L 63/107; H04L 67/10; H04L 67/1042; H04L 2101/69; H04W 4/80; H04W 76/14; H04W 84/18
See application file for complete search history.

(56) References Cited

U.S. PATENT DOCUMENTS

| | | | |
|---|---|---|---|
| 6,097,386 A | 8/2000 | Bardon et al. | |
| 6,137,499 A | 10/2000 | Tesler | |
| 6,204,763 B1* | 3/2001 | Sone | G06Q 10/087 340/5.1 |
| 6,301,579 B1 | 10/2001 | Becker | |
| 7,483,964 B1 | 1/2009 | Jackson | |
| 7,676,034 B1 | 3/2010 | Wu et al. | |
| 7,721,303 B2 | 5/2010 | Alves et al. | |
| 8,095,432 B1 | 1/2012 | Berman et al. | |
| 8,144,853 B1 | 3/2012 | Aboujaoude et al. | |
| 8,177,260 B2 | 5/2012 | Trooper et al. | |
| 8,463,939 B1 | 6/2013 | Galvin | |
| 8,686,924 B2 | 4/2014 | Braun et al. | |
| 8,908,926 B2 | 12/2014 | Henderson et al. | |
| 9,230,224 B2 | 1/2016 | Ramsey et al. | |
| 9,576,312 B2 | 2/2017 | Melcher et al. | |
| 9,886,710 B2 | 2/2018 | Melcher et al. | |
| 10,212,046 B2 | 2/2019 | Chang et al. | |
| 10,304,114 B2 | 5/2019 | Melcher et al. | |
| 10,453,111 B2 | 10/2019 | Melcher | |
| 11,100,561 B2 | 8/2021 | Melcher et al. | |
| 11,210,723 B2 | 12/2021 | Melcher et al. | |
| 11,657,443 B2 | 5/2023 | Melcher et al. | |
| 11,810,178 B2 | 11/2023 | Melcher et al. | |
| 2002/0149614 A1 | 10/2002 | Biebesheimer et al. | |
| 2002/0161664 A1 | 10/2002 | Shaya et al. | |
| 2003/0073412 A1 | 4/2003 | Meade, II | |
| 2003/0229895 A1 | 12/2003 | Jasinschi et al. | |
| 2004/0015714 A1* | 1/2004 | Abraham | G06Q 20/3821 726/4 |
| 2005/0131716 A1 | 6/2005 | Hanan et al. | |
| 2005/0131894 A1 | 6/2005 | Vuong | |
| 2006/0164324 A1 | 7/2006 | Polivy et al. | |
| 2007/0087313 A1 | 4/2007 | Vest | |
| 2007/0143250 A1 | 6/2007 | Zigon | |
| 2007/0143345 A1 | 6/2007 | Jones et al. | |
| 2007/0174331 A1 | 7/2007 | Wolf | |
| 2007/0244844 A1 | 10/2007 | Brinson et al. | |
| 2007/0299796 A1 | 12/2007 | Macbeth et al. | |
| 2008/0015953 A1 | 1/2008 | Harper et al. | |
| 2008/0092209 A1* | 4/2008 | Davis | G06F 21/32 726/2 |
| 2008/0092245 A1 | 4/2008 | Alward et al. | |
| 2008/0146334 A1 | 6/2008 | Kil | |
| 2008/0146343 A1 | 6/2008 | Sullivan et al. | |
| 2008/0158222 A1 | 7/2008 | Li et al. | |
| 2008/0183645 A1* | 7/2008 | Burger | H04L 67/1095 709/205 |
| 2008/0207220 A1 | 8/2008 | Aaron | |
| 2008/0222706 A1 | 9/2008 | Renaud et al. | |
| 2008/0250408 A1 | 10/2008 | Tsui et al. | |
| 2009/0006525 A1 | 1/2009 | Moore | |
| 2009/0044113 A1 | 2/2009 | Jones et al. | |
| 2009/0150203 A1 | 6/2009 | Baudisch et al. | |
| 2009/0254971 A1 | 10/2009 | Herz et al. | |
| 2009/0300516 A1 | 12/2009 | Jerrard-dunne et al. | |
| 2009/0309891 A1 | 12/2009 | Karkanias et al. | |
| 2010/0083139 A1 | 4/2010 | Dawson et al. | |
| 2010/0125632 A1 | 5/2010 | Leonard | |
| 2010/0128988 A1 | 5/2010 | Kincaid | |
| 2010/0153868 A1 | 6/2010 | Allen et al. | |
| 2010/0182935 A1 | 7/2010 | David | |
| 2010/0218101 A1 | 8/2010 | O'shaughnessy et al. | |
| 2010/0231418 A1 | 9/2010 | Whitlow et al. | |
| 2010/0315549 A1* | 12/2010 | Basso | H04N 21/4402 348/E7.003 |
| 2011/0015497 A1 | 1/2011 | Eggenberger et al. | |
| 2011/0046805 A1 | 2/2011 | Bedros et al. | |
| 2011/0093780 A1 | 4/2011 | Dunn | |
| 2011/0148916 A1 | 6/2011 | Blattner | |
| 2011/0153663 A1 | 6/2011 | Koren et al. | |
| 2011/0238482 A1 | 9/2011 | Carney et al. | |
| 2011/0295974 A1* | 12/2011 | Kashef | H04L 65/1094 709/217 |
| 2012/0014290 A1 | 1/2012 | David | |
| 2012/0059787 A1 | 3/2012 | Brown et al. | |
| 2012/0096076 A1 | 4/2012 | Chan | |
| 2012/0290978 A1 | 11/2012 | Devecka | |
| 2013/0006899 A1 | 1/2013 | Cook | |
| 2013/0007098 A1 | 1/2013 | Averbuch et al. | |
| 2013/0119255 A1 | 5/2013 | Dickinson et al. | |
| 2013/0122936 A1 | 5/2013 | Hudson et al. | |
| 2013/0173390 A1 | 7/2013 | Polo | |
| 2013/0214935 A1 | 8/2013 | Kim et al. | |
| 2013/0218511 A1 | 8/2013 | Mager et al. | |
| 2013/0238538 A1 | 9/2013 | Cook et al. | |
| 2013/0257876 A1 | 10/2013 | Davis | |
| 2013/0257877 A1 | 10/2013 | Davis | |
| 2013/0258118 A1 | 10/2013 | Felt | |
| 2013/0262588 A1 | 10/2013 | Barak et al. | |
| 2013/0275994 A1 | 10/2013 | Uola et al. | |
| 2013/0297688 A1 | 11/2013 | Zheng | |
| 2013/0305185 A1 | 11/2013 | Nicol, II et al. | |
| 2013/0321446 A1 | 12/2013 | Cutcher-gershenfeld et al. | |
| 2014/0032723 A1 | 1/2014 | Nema | |
| 2014/0135644 A1 | 5/2014 | Kim | |
| 2014/0136365 A1 | 5/2014 | Nista et al. | |
| 2014/0143682 A1 | 5/2014 | Druck | |
| 2014/0173078 A1 | 6/2014 | Mccord et al. | |
| 2014/0176335 A1 | 6/2014 | Brumback et al. | |
| 2014/0189829 A1 | 7/2014 | Mclachlan et al. | |
| 2014/0279294 A1 | 9/2014 | Field-darragh et al. | |
| 2014/0297395 A1 | 10/2014 | Chao et al. | |
| 2015/0018988 A1 | 1/2015 | Safar | |
| 2015/0032541 A1 | 1/2015 | Haddad et al. | |
| 2015/0088598 A1 | 3/2015 | Acharyya et al. | |
| 2015/0120555 A1 | 4/2015 | Jung et al. | |
| 2015/0127565 A1 | 5/2015 | Chevalier et al. | |
| 2015/0172742 A1* | 6/2015 | Richardson | H04N 21/4112 725/10 |
| 2015/0253445 A1 | 9/2015 | Luo et al. | |
| 2015/0262282 A1 | 9/2015 | Walti et al. | |
| 2015/0262458 A1 | 9/2015 | Faaborg et al. | |
| 2015/0269151 A1 | 9/2015 | Wallace | |

(56) References Cited

U.S. PATENT DOCUMENTS

| | | | |
|---|---|---|---|
| 2015/0278912 A1 | 10/2015 | Melcher et al. | |
| 2015/0279069 A1 | 10/2015 | Melcher et al. | |
| 2015/0281009 A1 | 10/2015 | Melcher et al. | |
| 2015/0281252 A1 | 10/2015 | Melcher et al. | |
| 2016/0012129 A1 | 1/2016 | Rampson et al. | |
| 2016/0048595 A1 | 2/2016 | Vanblon et al. | |
| 2016/0048993 A1 | 2/2016 | Shimomura et al. | |
| 2016/0049008 A1 | 2/2016 | Haddick et al. | |
| 2016/0270717 A1 | 9/2016 | Luna et al. | |
| 2017/0171901 A1 | 6/2017 | Melcher et al. | |
| 2018/0189858 A1 | 7/2018 | Melcher et al. | |
| 2019/0028338 A1* | 1/2019 | Kozura | H04W 12/069 |
| 2019/0069031 A1 | 2/2019 | Maher et al. | |
| 2019/0130629 A1 | 5/2019 | Chand et al. | |
| 2019/0385214 A1 | 12/2019 | Melcher et al. | |
| 2020/0013111 A1 | 1/2020 | Melcher et al. | |
| 2021/0082023 A9 | 3/2021 | Melcher et al. | |
| 2021/0350440 A1 | 11/2021 | Melcher et al. | |
| 2022/0092671 A1 | 3/2022 | Melcher et al. | |

FOREIGN PATENT DOCUMENTS

| | | |
|---|---|---|
| CN | 115496557 A | 12/2022 |
| JP | 2000296904 A | 10/2000 |
| JP | 2006525570 A | 11/2006 |
| KR | 20050025288 A | 3/2005 |
| KR | 20080091045 A | 10/2008 |
| KR | 20090086805 A | 8/2009 |
| KR | 20120019530 A | 3/2012 |
| KR | 1020130023365 A | 3/2013 |
| KR | 20130047808 | 5/2013 |
| KR | 20130068593 A | 6/2013 |
| KR | 101334066 B1 | 11/2013 |
| KR | 102153803 B1 | 9/2020 |
| KR | 102379643 B1 | 3/2022 |
| WO | WO-2009108439 A1 | 9/2009 |
| WO | WO-2012144776 A2 | 10/2012 |
| WO | WO-2012173446 A2 | 12/2012 |
| WO | WO-2015148559 A1 | 10/2015 |

OTHER PUBLICATIONS

U.S. Appl. No. 15/431,799, filed Feb. 14, 2017, Complementary Activity Based on Availability of Functionality.

U.S. Appl. No. 14/449,126 U.S. Pat. No. 10,304,114, filed Jul. 31, 2014, Data Mesh Based Environmental Augmentation.

U.S. Appl. No. 16/391,852 U.S. Pat. No. 11,210,723, filed Apr. 23, 2019, Data Mesh Based Environmental Augmentation.

U.S. Appl. No. 17/538,491 U.S. Pat. No. 11,657,443, filed Nov. 30, 2021, Data Mesh Based Environmental Augmentation.

U.S. Appl. No. 14/449,113 U.S. Pat. No. 9,886,710, filed Jul. 31, 2014, Data Mesh Visualization.

U.S. Appl. No. 15/848,351 U.S. Pat. No. 10,453,111, filed Dec. 20, 2017, Data Mesh Visualization.

U.S. Appl. No. 16/575,619 U.S. Pat. No. 11,100,561, filed Sep. 19, 2019, Data Mesh Visualization.

U.S. Appl. No. 17/369,183, filed Jul. 7, 2021, Data Mesh Visualization.

"U.S. Appl. No. 14/449,126 Non Final Office Action dated Oct. 23, 2015", 20 pgs.

"U.S. Appl. No. 14/449,113, Examiner Interview Summary dated Jun. 13, 2017", 4 pgs.

"U.S. Appl. No. 14/449,113, Final Office Action dated Aug. 4, 2016", 21 pgs.

"U.S. Appl. No. 14/449,113, Non Final Office Action dated Feb. 26, 2016", 15 pgs.

"U.S. Appl. No. 14/449,113, Non Final Office Action dated Mar. 3, 2017", 15 pgs.

"U.S. Appl. No. 14/449,113, Notice of Allowance dated Sep. 18, 2017", 7 pgs.

"U.S. Appl. No. 14/449,126, Examiner Interview Summary dated Mar. 21, 2017", 3 pgs.

"U.S. Appl. No. 14/449,126, Examiner Interview Summary dated Aug. 11, 2017", 2 pgs.

"U.S. Appl. No. 14/449,126, Examiner Interview Summary dated Sep. 22, 2016", 5 pgs.

"U.S. Appl. No. 14/449,126, Final Office Action dated Jun. 2, 2017", 22 pgs.

"U.S. Appl. No. 14/449,126, Final Office Action dated Jun. 17, 2016", 20 pgs.

"U.S. Appl. No. 14/449,126, Final Office Action dated Jul. 11, 2018", 30 pgs.

"U.S. Appl. No. 14/449,126, Non Final Office Action dated Nov. 16, 2017", 21 pgs.

"U.S. Appl. No. 14/449,126, Non Final Office Action dated Nov. 21, 2016", 20 pgs.

"U.S. Appl. No. 14/449,126, Notice of Allowance dated Jan. 9, 2019", 16 pgs.

"U.S. Appl. No. 14/459,115, Final Office Action dated Aug. 4, 2016", 31 pgs.

"U.S. Appl. No. 14/459,115, Non Final Office Action dated Feb. 26, 2016", 19 pgs.

"U.S. Appl. No. 14/498,326, Corrected Notice of Allowance dated Nov. 8, 2016", 2 pgs.

"U.S. Appl. No. 14/498,326, Corrected Notice of Allowance dated Dec. 16, 2016", 2 pgs.

"U.S. Appl. No. 14/498,326, First Action Interview—Office Action Summary dated Jun. 13, 2016", 5 pgs.

"U.S. Appl. No. 14/498,326, First Action Interview Pre-Interview Communication dated Feb. 2, 2016", 4 pgs.

"U.S. Appl. No. 14/498,326, Notice of Allowance dated Oct. 7, 2016", 16 pgs.

"U.S. Appl. No. 15/431,799, Advisory Action dated Sep. 20, 2018", 3 pages.

"U.S. Appl. No. 15/431,799, Examiner Interview Summary dated Aug. 7, 2019", 3 pgs.

"U.S. Appl. No. 15/431,799, Final Office Action dated Apr. 2, 2019", 17 pgs.

"U.S. Appl. No. 15/431,799, Final Office Action dated Jul. 12, 2018", 17 pgs.

"U.S. Appl. No. 15/431,799, Final Office Action dated Nov. 27, 2019", 25 pgs.

"U.S. Appl. No. 15/431,799, Non Final Office Action dated Jun. 13, 2019", 27 pgs.

"U.S. Appl. No. 15/431,799, Non Final Office Action dated Nov. 1, 2018", 18 pgs.

"U.S. Appl. No. 15/431,799, Non Final Office Action dated Dec. 29, 2017", 15 pgs.

"U.S. Appl. No. 15/431,799, Preliminary Amendment filed Mar. 2, 2017", 9 pgs.

"U.S. Appl. No. 15/431,799, Response filed Jan. 22, 2020 to Final Office Action dated Nov. 27, 2019", 11 pgs.

"U.S. Appl. No. 15/848,351, Examiner Interview Summary dated Aug. 13, 2019", 3 pgs.

"U.S. Appl. No. 15/848,351, Non Final Office Action dated Feb. 25, 2019", 13 pgs.

"U.S. Appl. No. 15/848,351, Notice of Allowance dated Jun. 12, 2019", 8 pgs.

"U.S. Appl. No. 15/848,351, Preliminary Amendment filed Mar. 23, 2018", 7 pgs.

"U.S. Appl. No. 16/391,852, Corrected Notice of Allowability dated Aug. 31, 2021", 2 pgs.

"U.S. Appl. No. 16/391,852, Corrected Notice of Allowability dated Sep. 9, 2021", 2 pgs.

"U.S. Appl. No. 16/391,852, Examiner Interview Summary dated Jan. 21, 2021", 2 pgs.

"U.S. Appl. No. 16/391,852, Examiner Interview Summary dated Jul. 14, 2021", 2 pgs.

"U.S. Appl. No. 16/391,852, Final Office Action dated Apr. 13, 2021", 14 pgs.

"U.S. Appl. No. 16/391,852, Non Final Office Action dated Oct. 13, 2020", 13 pgs.

(56) References Cited

OTHER PUBLICATIONS

"U.S. Appl. No. 16/391,852, Notice of Allowance dated Aug. 20, 2021", 18 pgs.
"U.S. Appl. No. 16/391,852, Preliminary Amendment Filed Sep. 9, 2019", 7 pgs.
"U.S. Appl. No. 16/391,852, Response filed Jan. 13, 2021 to Non Final Office Action dated Oct. 13, 2020", 14 pgs.
"U.S. Appl. No. 16/575,619, Corrected Notice of Allowability dated May 21, 2021", 2 pgs.
"U.S. Appl. No. 16/575,619, Corrected Notice of Allowability dated Jun. 28, 2021", 2 pgs.
"U.S. Appl. No. 16/575,619, Corrected Notice of Allowability dated Jul. 22, 2021", 2 pgs.
"U.S. Appl. No. 16/575,619, Non Final Office Action dated Dec. 16, 2020", 10 pgs.
"U.S. Appl. No. 16/575,619, Notice of Allowance dated Apr. 19, 2021", 7 pgs.
"U.S. Appl. No. 17/369,183, Advisory Action dated Apr. 28, 2023", 2 pgs.
"U.S. Appl. No. 17/369,183, Examiner Interview Summary dated Apr. 20, 2023", 2 pgs.
"U.S. Appl. No. 17/369,183, Examiner Interview Summary dated Nov. 15, 2022", 2 pgs.
"U.S. Appl. No. 17/369,183, Final Office Action dated Feb. 21, 2023", 12 pgs.
"U.S. Appl. No. 17/369,183, Non Final Office Action dated Sep. 6, 2022", 11 pgs.
"U.S. Appl. No. 17/369,183, Notice of Allowance dated Jun. 27, 2023", 7 pgs.
"U.S. Appl. No. 17/369,183, Preliminary Amendment filed Jul. 29, 2021", 7 pages.
"U.S. Appl. No. 17/538,491, Corrected Notice of Allowability dated Apr. 20, 2023", 2 pgs.
"U.S. Appl. No. 17/538,491, Notice of Allowance dated Jan. 17, 2023", 18 pgs.
"Chinese Application Serial No. 201580027971.8, Decision of Rejection dated May 7, 2020", With English machine translation, 38 pgs.
"Chinese Application Serial No. 201580027971.8, Office Action dated Jan. 30, 2019", With English translation, 36 pgs.
"Chinese Application Serial No. 201580027971.8, Office Action dated Jul. 17, 2019", With English translation, 34 pgs.
"Chinese Application Serial No. 201580027971.8, Office Action dated Dec. 26, 2019", w/o English translation, 3 pgs.
"Examiner-Initiated Interview Summary received for U.S. Appl. No. 15/431,799, dated Sep. 20, 2018", (Sep. 20, 2018), 1 page.
"International Application Serial No. PCT/US2015/022318, International Preliminary Report on Patentability dated Oct. 7, 2016", 9 pgs.
"International Application Serial No. PCT/US2015/022318, International Search Report dated Jul. 1, 2015", 2 pgs.
"International Application Serial No. PCT/US2015/022318, Written Opinion dated Jul. 1, 2015", 11 pgs.
"Korean Application Serial No. 10-2018-7012784, Notice of Preliminary Rejection dated Mar. 29, 2019", (w/English Translation), 4 pages.
"Korean Application Serial No. 10-2018-7012784, Notice of Preliminary Rejection dated Jul. 15, 2019", With English machine translation, 19 pgs.
"Korean Application Serial No. 10-2018-7012784, Notice of Preliminary Rejection dated Oct. 2, 2018", (w/English Translation), 7 pages.
"Korean Application Serial No. 10-2018-7012784, Notice of Preliminary Rejection dated Nov. 21, 2019", w/ English Translation, 14 pgs.
"Korean Application Serial No. 10-2018-7012784, Office Action dated Mar. 9, 2020", With English machine translation, 11 pgs.
"Korean Application Serial No. 10-2018-7012784, Response filed May 29, 2019 to Notice of Preliminary Rejection dated Mar. 29, 2019", w/ English Claims, 17 pgs.
"Korean Application Serial No. 10-2022-7009425, Final Office Action dated Mar. 30, 2023", With English machine translation, 9 pgs.
"Korean Application Serial No. 10-2022-7009425, Notice of Preliminary Rejection dated Aug. 30, 2022", With English machine translation, 10 pgs.
"Korean Application Serial No. 2016-7029553, Final Office Action dated Nov. 30, 2017", With English Translation, 4 pgs.
"Korean Application Serial No. 2016-7029553, Office Action dated Mar. 5, 2018", with English Claims, 10 pgs.
"Korean Application Serial No. 2016-7029553, Office Action dated May 18, 2017", with English translation of claims, 13 pgs.
"Korean Application Serial No. 2016-7029553, Response filed Jan. 30, 2018 to Final Office Action dated Nov. 30, 2017", W/ English Translation, 34 pgs.
"Korean Application Serial No. 2016-7029553, Response filed Jul. 18, 2017 to Office Action dated May 18, 2017", with English translation of claims, 29 pgs.
"Korean Application Serial No. 2020-7025223, Notice of Preliminary Rejection dated Jun. 21, 2021", With English machine translation, 15 pgs.
"Korean Application Serial No. 2020-7025223, Notice of Preliminary Rejection dated Oct. 6, 2020", w/ English translation, 9 pgs.
"Response to Non-Final Office Action filed on Apr. 3, 2018, for U.S. Appl. No. 14/449,126, dated Nov. 16, 2017", (Apr. 3, 2018), 17 pages.
Bachvarov, A., et al., "Immersive Representation of Objects in Virtual Reality Environment Implementing Impicit Properties", Developments in Esystems Engineering, (2011), pp. 587-592.
Chen, et al., "Real-time smartphone sensing and recommendations towards context-awareness shopping", Springer-Verlag Berlin Heidelberg 2013, (Dec. 6, 2013), 61-72.
Dinh, El, et al., "Implementation of a Physical Activity Monitoring System for the Elderly People With Built-in Vital Sign and Fall Detection", IEEE, Sixth International Conference on Information Technology: New Generations, (Aug. 2009), 1-6.
Lynggaard Ph.D, "Artificial intelligence and Internet of Things in a "smart home" context: A Distributed System Architecture", Department of Electronic Systems, Aalborg University, (Mar. 13, 2014), 1-285.
Metin, Akay, "Perceptualization of Biomedical Data, Information Technologies in Medicine", vol. 1: Medical Simulation and Education, (2001), pp. 189-204.
Park, et al., "Design patterns for context-aware services", Springer Science+Business Media New York 2014, Multimed Tools Appl (2015) 74:2337-2358 DOI 10.1007/s11042-014-2001-7, (Apr. 23, 2014), 22 pgs.
Park, et al., "Location-Based Recommendation System Using Bayesian User's Preference Modelin Mobile Devices", Springer-Verlag Berlin Heidelberg 2007UIC 2007, LNCS 4611, (2007), 1130-1139.
Ping Yu, et al., "Application mobility in pervasive computing a survey", 16 pgs.
Santos, Rodrigues Dos Selan, et al., "Using a Rendering Engine to Support the Development of Immersive Virtual Reality Applications", Human-Computer Interfaces, and Measurement Systems, (Jul. 2008), 6 pages.
Yeh, et al., "Intelligent service-integrated platform based on the RFID technology and software agent system", journal homepage: www.elsevier.com/locate/eswa, Elsevier L TO, vol. 38, Issue 4, (Apr. 2011), 3058-3068.
Yu, Ping, et al., "Pervasive and Mobile Computing", (2013), 16 pages.
"Korean Application Serial No. 10-2022-7009425, Notice of Preliminary Rejection dated Aug. 30, 2023", With English translation, 11 pages.

* cited by examiner

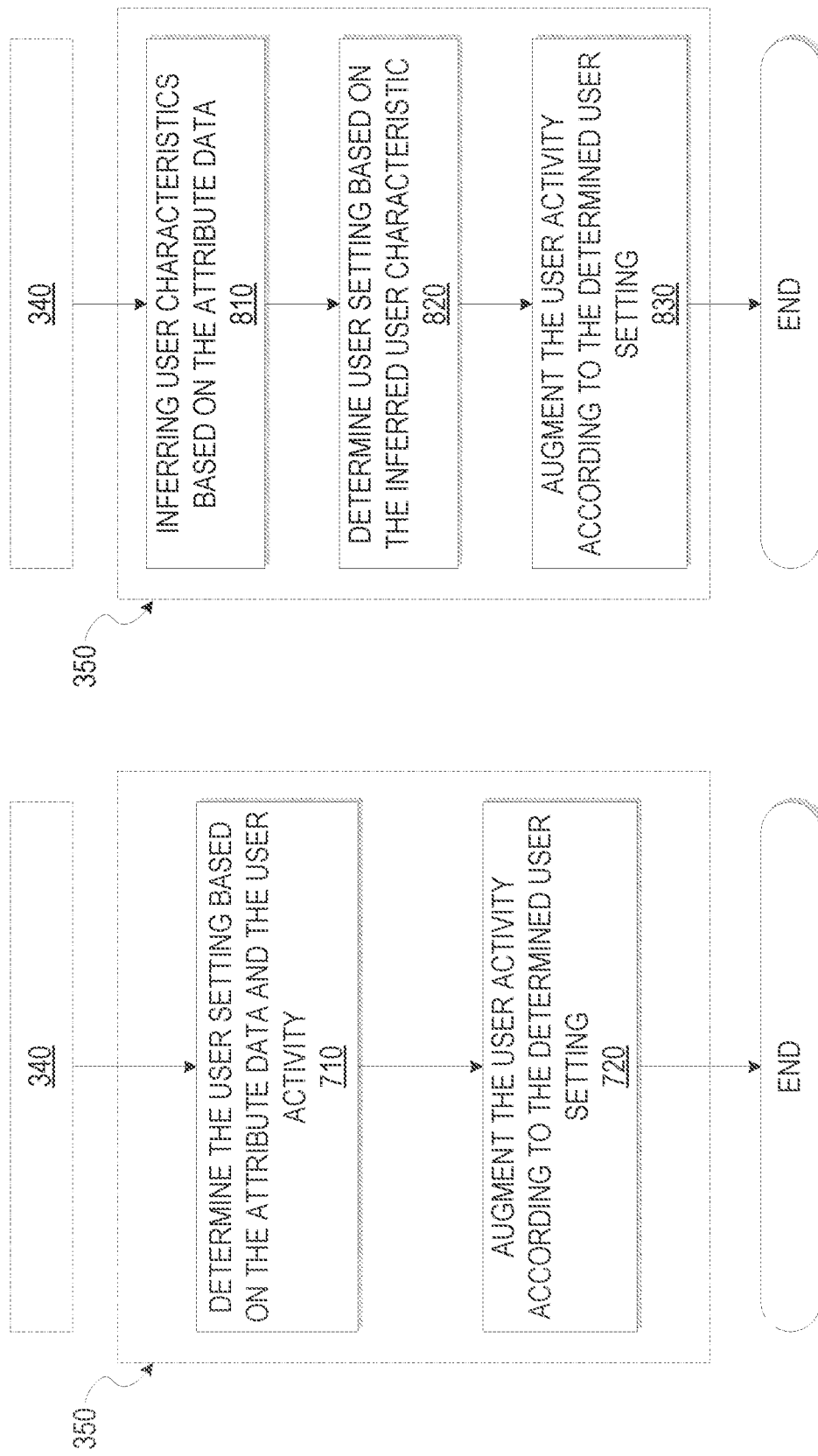

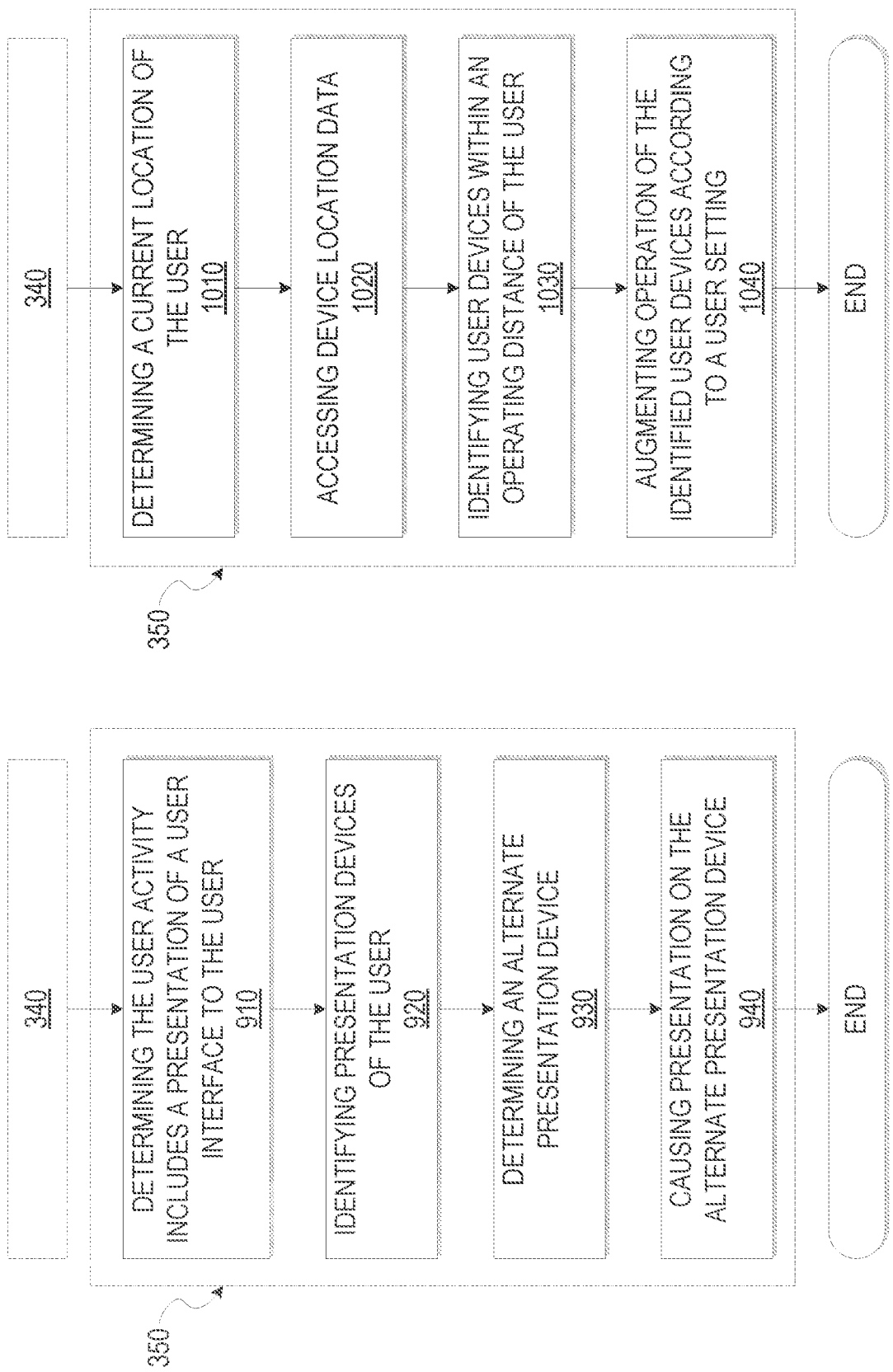

1800

DEVICE 1722
- DEVICE ID
- DEVICE NAME
- RESOURCES
- I/O COMPONENT DATA

POSITION DATA 1804
- LOCATION DATA
- ORIENTATION DATA
- BEACON DETECTIONS

LOCATION DATA 1806
- LATITUDE
- LONGITUDE
- ALTITUDE
- TIME STAMP

MOTION DATA 1808
- ACCELERATION IN X, Y, AND Z AXES
- VELOCITY
- ANGULAR ACCELERATION

ENVIRONMENTAL DATA 1810
- AMBIENT TEMPERATURE
- ATMOSPHERIC PRESSURE
- LUMINOSITY
- ACOUSTIC DECIBEL LEVEL

○ ○ ○

BIOMETRIC DATA 1812
- BLOOD PRESSURE
- HEART RATE
- GLUCOSE LEVEL
- BODY TEMPERATURE

STANDARD DEVICE PARAMETERS 1802
- aliveTime (sec)
- batteryLevel (integer %)
- batteryVoltage (Volts)
- current (Amps)
- currentBillingRate (Money)
- daylLghtSavingsTime (boolean)
- dimmerValue (integer)
- accumluatedEnergy (Wh)
- deviceIdentify (sec; noise/blink. etc.)
- illuminance (lux)
- InternalURLOfDevice (string)
- model (string)
- outletStatus (string; ON/OFF)
- packetErrorRateForServicibility (int)
- power (Watts)
- measuredPowerFactor (pf)
- uploadInterval (sec)
- accumulatedEnergy (VArh)
- numberOfReboots (int)
- timeToReboot (sec)
- receiverSignalStrengthIndicator (dBm)
- signalStrentgh (int; 0-100%)
- temp (degrees Fahrenheit )
- targetTempCool (degrees Fahrenheit )
- targetTempHeat (degrees Fahrenheit )
- measuredVoltage (Volts)
- timeZone (minutes from UTC)

*FIG. 18*

DATA MESH BASED ENVIRONMENTAL AUGMENTATION

RELATED APPLICATIONS

This application is a continuation of and claims the benefit of priority of U.S. application Ser. No. 17/538,491, filed Nov. 30, 2021, which is a continuation of and claims the benefit of priority of U.S. application Ser. No. 16/391,852, filed Apr. 23, 2019, which is a continuation of and claims the benefit of priority of U.S. application Ser. No. 14/449,126, filed Jul. 31, 2014, which claims the priority benefit of U.S. Provisional Application No. 61/970,263, filed Mar. 25, 2014, each of which is hereby incorporated by reference in its entirety.

TECHNICAL FIELD

Embodiments of the present disclosure relate generally to mobile device technology and, more particularly, but not by way of limitation, to data mesh based environmental augmentation.

BACKGROUND

In recent years mobile devices, wearable devices, smart devices, and the like have pervaded nearly every aspect of modern life. Such devices are increasingly incorporating sensors to monitor everything from the moisture level of houseplants to the dribbling of a basketball. Network connected devices like these are capable of providing a near real-time and constant data feed. These trends have provided a vast amount of rich, constantly updated data.

BRIEF DESCRIPTION OF THE DRAWINGS

Various ones of the appended drawings merely illustrate example embodiments of the present disclosure and cannot be considered as limiting its scope.

FIGS. 7-10 are flow diagrams illustrating further example operations of the method of FIG. 3, according to some example embodiments.

FIG. 18 is a block diagram of an example data structure for example attribute data associated with a device, according to some example embodiments.

Figure 1:
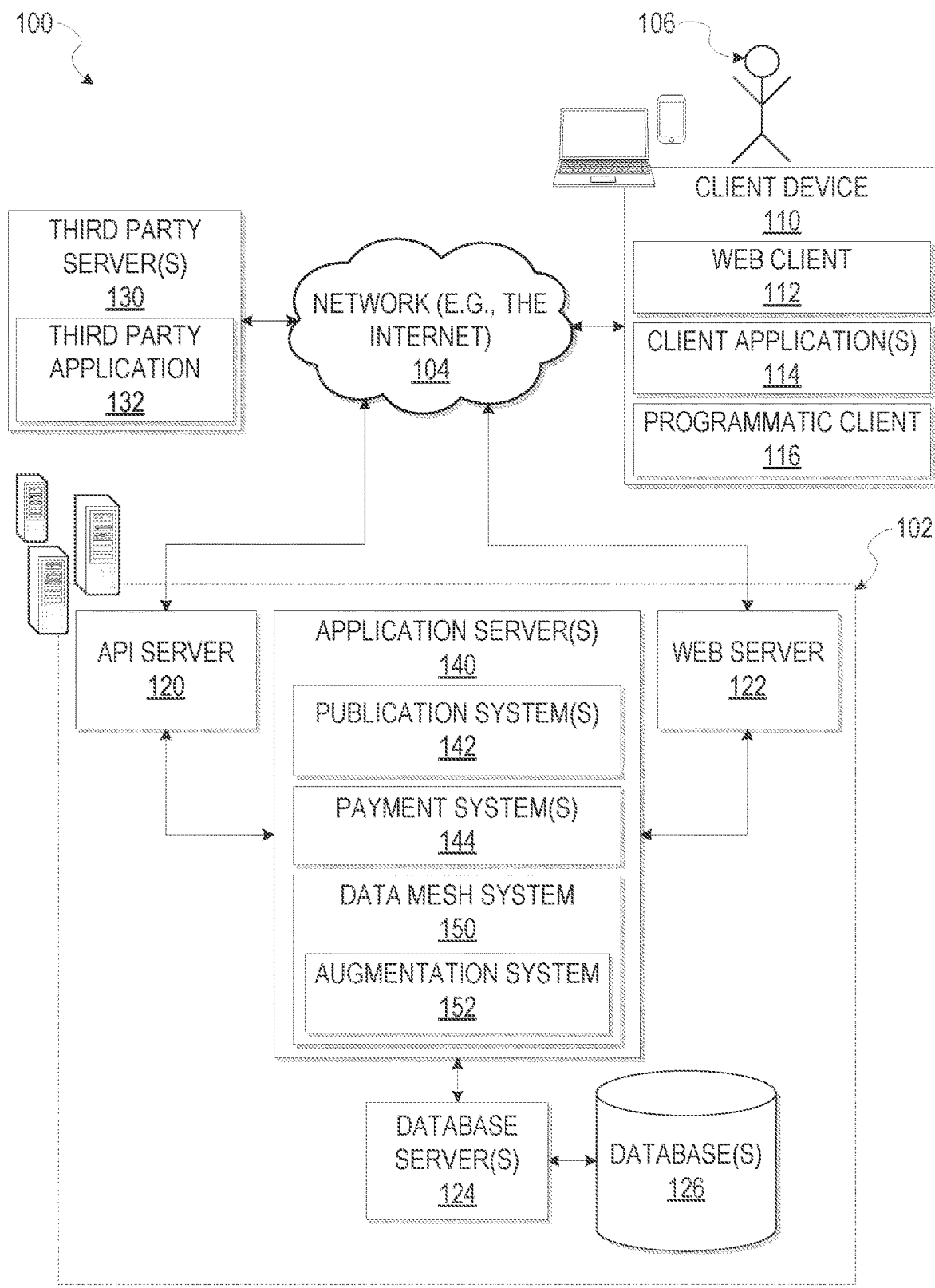
FIG. 1 is a block diagram illustrating a networked system, according to some example embodiments.

The headings provided herein are merely for convenience and do not necessarily affect the scope or meaning of the terms used.

DETAILED DESCRIPTION

The description that follows includes systems, methods, techniques, instruction sequences, and computing machine program products that embody illustrative embodiments of the disclosure. In the following description, for the purposes of explanation, numerous specific details are set forth in order to provide an understanding of various embodiments of the inventive subject matter. It will be evident, however, to those skilled in the art, that embodiments of the inventive subject matter may be practiced without these specific details. In general, well-known instruction instances, protocols, structures, and techniques are not necessarily shown in detail.

In various example embodiments, attribute data, including real-time data, may be received from a plurality of attribute sources, a user may be authenticated based on an analysis of the attribute data, a user activity may be identified based on the attribute data, and the user activity may be augmented according to a user setting. The attribute data may include data received from a broad gamut of attribute sources such as, for example, from mobile devices, smart devices, smart homes, social network services, user profiles, browsing histories, purchase histories, and so forth.

Subsequent to receiving the attribute data, a portion of the real-time data indicative of an identity of the user may be identified. For example, the real-time data may include a location of a mobile device of the user, sensor data from a device of the user, and so on. In an example embodiment, the identity of the user may be authenticated based on an analysis of the identified portion of the real-time data. For instance, the location of the user mobile device may be indicative of the location of the user, and if the location of the user device is within a distance of an Internet device currently being used, it may be inferred that the user may be currently using the Internet device. Many other indications of the user's identity may be employed to authenticate the identity of the user. In further example embodiments, an identity likelihood metric may be calculated based on an analysis of the attribute data. In some example embodiments, the identity of the user may be authenticated when the identity likelihood metric exceeds a threshold.

In still further example embodiments, based on authenticating the identity of the user, a user activity being performed by the user may be identified based on the real-time data. For example, the user may be using a website, jogging, entering a room (e.g., walking from a living room to a kitchen), and so on. The user activity may be augmented according to the user setting. In a specific example, the user may be using a website that implements a login, and based on the authentication of the user identity, the security for the website login may be reduced or the user is automatically logged in. In another specific example, the user may be streaming media in the living room to an Internet-connected device (e.g., a media entertainment system presenting to a display), and the streaming may be continued in the kitchen (e.g., to a smart refrigerator that includes a display) when the user moves from the living room to the kitchen. Many other user activities may be augmented in a variety of ways.

With reference to FIG. 1, an example embodiment of a high-level client-server-based network architecture 100 is shown. A networked system 102 provides server-side functionality via a network 104 (e.g., the Internet or wide area network (WAN)) to a client device 110. A user (e.g., user 106) may interact with the networked system 102 using the client device 110. FIG. 1 illustrates, for example, a web client 112 (e.g., a browser, such as the Internet Explorer® browser developed by Microsoft® Corporation of Redmond, Washington State), client application(s) 114, and a programmatic client 116 executing on the client device 110. The client device 110 may include the web client 112, the client application(s) 114, and the programmatic client 116 alone, together, or in any suitable combination. Although FIG. 1 shows one client device 110, multiple client devices may be included in the network architecture 100.

The client device 110 may comprise a computing device that includes at least a display and communication capabilities that provide access to the networked system 102 via the network 104. The client device 110 may comprise, but is not limited to, a remote device, work station, computer, general purpose computer, Internet appliance, hand-held device, wireless device, portable device, wearable computer, cellular or mobile phone, personal digital assistant (PDA), smart phone, tablet, ultrabook, netbook, laptop, desktop, multi-processor system, microprocessor-based or programmable consumer electronic, game consoles, set-top box, network PC, mini-computer, and the like. In further example embodiments, the client device 110 may comprise one or more of a touch screen, accelerometer, gyroscope, biometric sensor, camera, microphone, global positioning system (GPS) device, and the like.

The client device 110 may communicate with the network 104 via a wired or wireless connection. For example, one or more portions of the network 104 may be an ad hoc network, an intranet, an extranet, a Virtual Private Network (VPN), a Local Area Network (LAN), a wireless LAN (WLAN), a Wide Area Network (WAN), a wireless WAN (WWAN), a Metropolitan Area Network (MAN), a portion of the Internet, a portion of the Public Switched Telephone Network (PSTN), a cellular telephone network, a wireless network, a Wireless Fidelity (Wi-Fi®) network, a Worldwide Interoperability for Microwave Access (WiMax) network, another type of network, or a combination of two or more such networks.

The client device 110 may include one or more of the applications (also referred to as "apps") such as, but not limited to, web browsers, book reader apps (operable to read e-books), media apps (operable to present various media forms including audio and video), fitness apps, biometric monitoring apps, messaging apps, electronic mail (email) apps, e-commerce site apps (also referred to as "marketplace apps"), and so on. The client application(s) 114 may include various components operable to present information to the user and communicate with networked system 102. In some embodiments, if the e-commerce site application is included in the client device 110, then this application may be configured to locally provide the user interface and at least some of the functionalities with the application configured to communicate with the networked system 102, on an as needed basis, for data or processing capabilities not locally available (e.g., access to a database of items available for sale, to authenticate a user, to verify a method of payment). Conversely, if the e-commerce site application is not included in the client device 110, the client device 110 may use its web browser to access the e-commerce site (or a variant thereof) hosted on the networked system 102.

In various example embodiments, the users (e.g., the user 106) may be a person, a machine, or other means of interacting with the client device 110. In some example embodiments, the users may not be part of the network architecture 100, but may interact with the network architecture 100 via the client device 110 or another means. For instance, the users may interact with client device 110 that may be operable to receive input information from (e.g., using touch screen input or alphanumeric input) and present information to (e.g., using graphical presentation on a device display) the users. In this instance, the users may, for example, provide input information to the client device 110 that may be communicated to the networked system 102 via the network 104. The networked system 102 may, in response to the received input information, communicate information to the client device 110 via the network 104 to be presented to the users. In this way, the user may interact with the networked system 102 using the client device 110.

An Application Program Interface (API) server 120 and a web server 122 may be coupled to, and provide programmatic and web interfaces respectively to, one or more application server(s) 140. The application server(s) 140 may host one or more publication system(s) 142, payment system(s) 144, and a data mesh system 150, each of which may comprise one or more modules or applications and each of which may be embodied as hardware, software, firmware, or any combination thereof. The application server(s) 140 are, in turn, shown to be coupled to one or more database server(s) 124 that facilitate access to one or more information storage repositories or database(s) 126. In an example embodiment, the database(s) 126 are storage devices that store information to be posted (e.g., publications or listings) to the publication system(s) 142. The database(s) 126 may also store digital goods information in accordance with some example embodiments.

Additionally, a third party application 132, executing on a third party server 130, is shown as having programmatic access to the networked system 102 via the programmatic interface provided by the API server 120. For example, the third party application 132, utilizing information retrieved from the networked system 102, may support one or more features or functions on a website hosted by the third party. The third party website may, for example, provide one or more promotional, marketplace, or payment functions that are supported by the relevant applications of the networked system 102.

The publication system(s) 142 may provide a number of publication functions and services to the users that access the networked system 102. The payment system(s) 144 may likewise provide a number of functions to perform or facilitate payments and transactions. While the publication system(s) 142 and payment system(s) 144 are shown in FIG. 1 to both form part of the networked system 102, it will be appreciated that, in alternative embodiments, each system 142 and 144 may form part of a payment service that is separate and distinct from the networked system 102. In some example embodiments, the payment system(s) 144 may form part of the publication system(s) 142.

The data mesh system 150 may provide functionality to receive, retrieve, or store a broad spectrum of data associated with the user. It will be noted that the collective, aggregated attribute data may be referred to as a "data mesh." The data mesh system 150 may store, for example, received data in storage devices such as the database(s) 126. In an example embodiment, the data mesh system 150 may include an augmentation system 152 that authenticates the user based on the attribute data, identifies a user activity being performed by the user, and augments the user activity according to a user preference. In some example embodiments, the data mesh system 150 may communicate with the client device 110, the third party server(s) 130, the publication system(s) 142 (e.g., retrieving listings), and the payment system(s) 144 (e.g., purchasing a listing). In an alternative example embodiment, the data mesh system 150 may be a part of the publication system(s) 142.

Further, while the client-server-based network architecture 100 shown in FIG. 1 employs a client-server architecture, the present inventive subject matter is, of course, not limited to such an architecture, and may equally well find application in a distributed, or peer-to-peer, architecture system, for example. The various systems of the applications server(s) 140 (e.g., the publication system(s) 142 and the payment system(s) 144) may also be implemented as stand-alone software programs, which do not necessarily have networking capabilities.

The web client 112 may access the various systems of the networked system 102 (e.g., the publication system(s) 142) via the web interface supported by the web server 122. Similarly, the programmatic client 116 and client application(s) 114 may access the various services and functions provided by the networked system 102 via the programmatic interface provided by the API server 120. The programmatic client 116 may, for example, be a seller application (e.g., the Turbo Lister application developed by eBay® Inc., of San Jose, California) to enable sellers to author and manage listings on the networked system 102 in an off-line manner, and to perform batch-mode communications between the programmatic client 116 and the networked system 102.

Figure 2A:
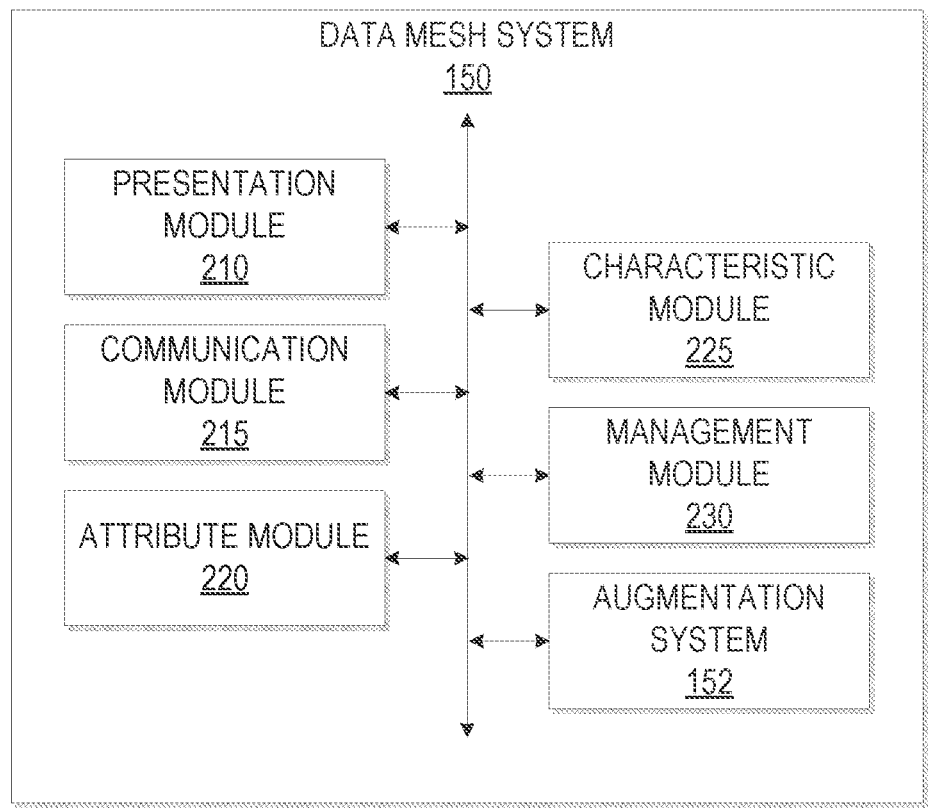
FIG. 2A is a block diagram illustrating an example embodiment of a data mesh system, according to some example embodiments.
Figure 2B:
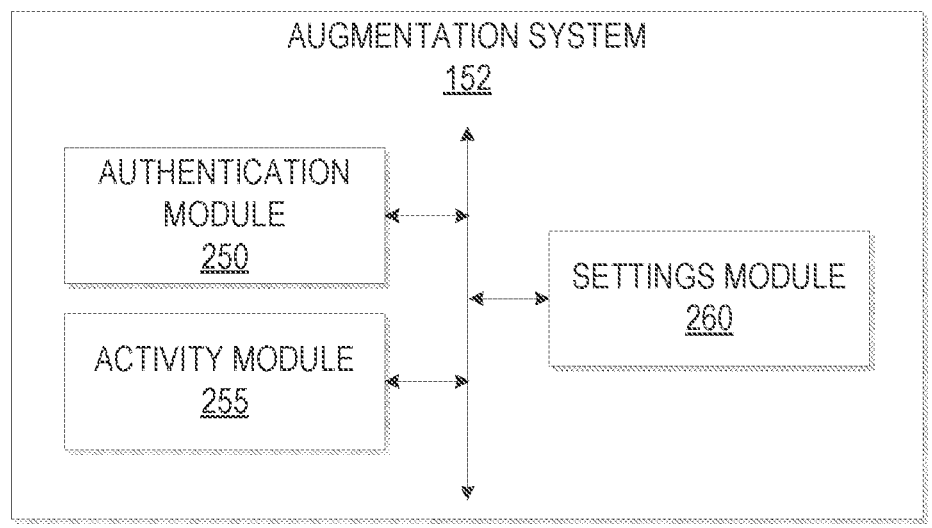
FIG. 2B is a block diagram illustrating an example embodiment of an augmentation system, according to some example embodiments.

FIG. 2A is a block diagram of the data mesh system 150, which may provide functionality to receive, retrieve, or access attribute data from attribute sources, analyze the attribute data, manage the attribute data, and so forth. In an example embodiment, the data mesh system 150 may include a presentation module 210, a communication module 215, an attribute module 220, a characteristic module 225, a management module 230, and the augmentation system 152. FIG. 2B is a block diagram of the augmentation system 152, which may provide functionality to authenticate the identity of the user, identify the user activity, and augment the user activity. The augmentation system 152 may include an authentication module 250, an activity module 255, and a settings module 260. All, or some, of the modules 210-260 of FIGS. 2A and 2B, may communicate with each other, for example, via a network coupling, shared memory, and the like. It will be appreciated that each module of modules 210-260 may be implemented as a single module, combined into other modules, or further subdivided into multiple modules. It will further be appreciated that the modules or functionality of the augmentation system 152 may be implemented in the data mesh system 150 and the modules or functionality of the data mesh system 150 may be implemented in the augmentation system 152. Other modules not pertinent to example embodiments may also be included, but are not shown.

Referring to FIG. 2A, the presentation module 210 may provide various presentation and user interface functionality operable to interactively present and receive information from users. For example, the presentation module 210 may cause presentation of various user interfaces to the user to facilitate augmenting the user activity. The presentation module 210 may present or cause presentation of information using a variety of means including visually displaying information and using other device outputs (e.g., acoustic, haptic). Interactively presenting is intended to include the exchange of information between a device and a user. The user may provide input to interact with the user interface in a variety of ways including alphanumeric input, cursor input, tactile input, or other input (e.g., one or more touch screen, camera, tactile sensors, light sensors, infrared sensors, biometric sensors, microphone, gyroscope, accelerometer, or other sensors). It will be appreciated that the presentation module 210 may provide many other user interfaces to facilitate functionality described herein. Further, it will be appreciated that "presenting" as used herein is intended to include communicating information to another device with functionality operable to perform presentation using the communicated information.

The communication module 215 may provide various communications functionality and web services. For example, network communication such as communicating with the networked system 102, the client device 110, and the third party server(s) 130 may be provided. In various example embodiments, the network communication may operate over wired or wireless modalities. Web services are intended to include retrieving information from the third party server(s) 130, the database(s) 126, and the application server(s) 140. Information retrieved by the communication module 215 may comprise data associated with the user (e.g., user profile information from an online account, social network service data associated with the user), data associated with one or more items listed on an e-commerce website (e.g., images of the item, reviews of the item, item price), or other data to facilitate the functionality described herein.

The attribute module 220 may receive, access, or retrieve a wide variety of attribute data from many different attribute sources. For example, the attribute module 220 may receive, retrieve, or access the attribute data from user devices or machines (e.g., the client device 110), social network services, the third party server(s) 130, the publication system(s) 142, the payment system(s) 144, other applications servers, or other attribute sources. The attribute data, as used herein, is intended to include raw data such as sensor data, profile data, social network content, and so on.

In some example embodiments, the attribute module 220 may extract the attribute data from various sources. For instance, a payment history log of the user may include a tremendous amount of extraneous data. The attribute module 220 may extract purchase information such as item purchased, time, purchase price, seller, location, brand, and so forth from the payment history log of the user.

In further example embodiments, the attribute module 220 may perform various functions to prepare or condition the attribute data for analysis. For instance, the attribute module 220 may standardize the attribute data to facilitate analysis of the attribute data (e.g., determine a normal form for the data to allow for comparison and other mathematical analysis). The attribute module 220 may perform many other functions to prepare the attribute data for analysis.

In various example embodiments, the attribute module 220 may store the attribute data in association with the user for subsequent analysis. For example, the attribute module 220 may store the attribute data in the database(s) 126. The attribute data may be stored in conjunction with a user identifier such that the attribute module 220 may subsequently use the user identifier to access the attribute data corresponding to a particular user. The attribute module 220 may access the stored attribute data using other schemes. For instance, the attribute module 220 may access a portion of the attribute data associated with a time, an item, a user, a type of user, a particular attribute source, and so forth. In this way, the attribute module 220 may access a portion of attribute data according to various parameters from among a large quantity of the attribute data to access, identify, or find pertinent and relevant data.

The characteristic module 225 may infer a user characteristic or multiple user characteristics corresponding to the user based on an analysis of at least a portion of the attribute data. Many schemes and techniques may be employed to infer the characteristic from the attribute data. For example, a particular user characteristic may be a work location of the user. The attribute data may include a plurality of locations (e.g., as determined by a GPS component of a user device used by the user) that include time stamps. The work location of the user may be inferred based on the consistency and timing of the locations included in the attribute data (e.g., during normal working hours, the user is typically at a particular office building). Many different portions of attribute data and combinations of portions of attribute data may be analyzed to infer a wide variety of characteristics.

In various example embodiments, characteristics (e.g., the user characteristics), as used herein, are intended to include traits, qualities, actions, activities, attitudes, habits, behaviors, and the like pertaining to a person or people. Inasmuch as the attribute data may not necessarily pertain to a person (e.g., raw data such as coordinates of a particular location), a characteristic (e.g., current location of the user, disliking spicy food, having young children, being a Star Trek fanatic) may be distinct from the attribute data.

The management module 230 may provide management functions associated with the attribute data. For example, the management module 230 may provide the user with functionality to edit, modify, update, or otherwise control the attribute data. For instance, the user may remove undesired attribute data via the functionality provided by the management module 230. In a further instance, the user may specify permissions for portions of the attribute data using the functionality provided by the management module 230. The permissions may allow or prohibit certain access or uses for the attribute data (e.g., the permission may prohibit access to the attribute data by third parties). The user may grant various levels of access and abilities. In some example embodiments, the permissions may persist for a period of time, and after expiration of the time period, the management module 230 may revoke the permissions.

In further example embodiments, the management module 230 may request consent from the user to access portions of the attribute data or to request permission for certain uses of the attribute data. For example, the management module 230 may request consent from the user to allow third parties to access portions of the attribute data. The management module 230 may request a variety of other consents associated with various actions corresponding to the attribute data.

In still further example embodiments, the management module 230 may provide functionality to allow third parties to access the attribute data or the user characteristics. For example, the management module 230 may provide a set of APIs that may be invoked by third parties to access the attribute data or the user characteristics. As discussed above, in some example embodiments, the management module 230 may determine permission or consent of the user prior to providing access to the attribute data.

Referring now to FIG. 2B, the authentication module 250 in the augmentation system 152 may provide functionality to facilitate authenticating a user's identity. For example, the authentication module 250 may identify a portion of the attribute data indicative of the identity of the user. Subsequently, the authentication module 250 may authenticate the identity of the user by analyzing the identified portion of the attribute data. In further example embodiments, the authentication module 250 may calculate an identity likelihood metric based on real-time data included in the attribute data. The identity likelihood metric may indicate the likelihood of authenticating the identity of the user (e.g., a higher identity likelihood metric may indicate a strong probability that the user's identity may be authenticated). The authentication module 250 may analyze a variety of portions of the attribute data using many different schemes and techniques to authenticate the identity of the user.

The activity module 255 may provide functionality associated with user activities. For example, the activity module 255 may identify a user activity being performed by the user based on the attribute data included in the real-time data. In a further example, the activity module 255 may facilitate augmentation of the identified user activity according to a user setting or user preference. For instance, the user setting may be associated with presenting information to the user (e.g., the user may have a desire to use a larger screen for presenting information if available). In this instance, the activity module 255 may augment presentation of information to the user based on the user setting.

The settings module 260 may provide functionality to access or determine one or more user settings. For example, the settings module 260 may determine the user setting based on the attribute data and the identified user activity. In some example embodiments, the settings module 260 may access the user setting from a storage device (e.g., the database(s) 126). In further example embodiments, the settings module 260 may determine the user setting based on an analysis of the user characteristics, similar users, a augmentation result from augmenting the user activity, and so forth.

Figure 3:
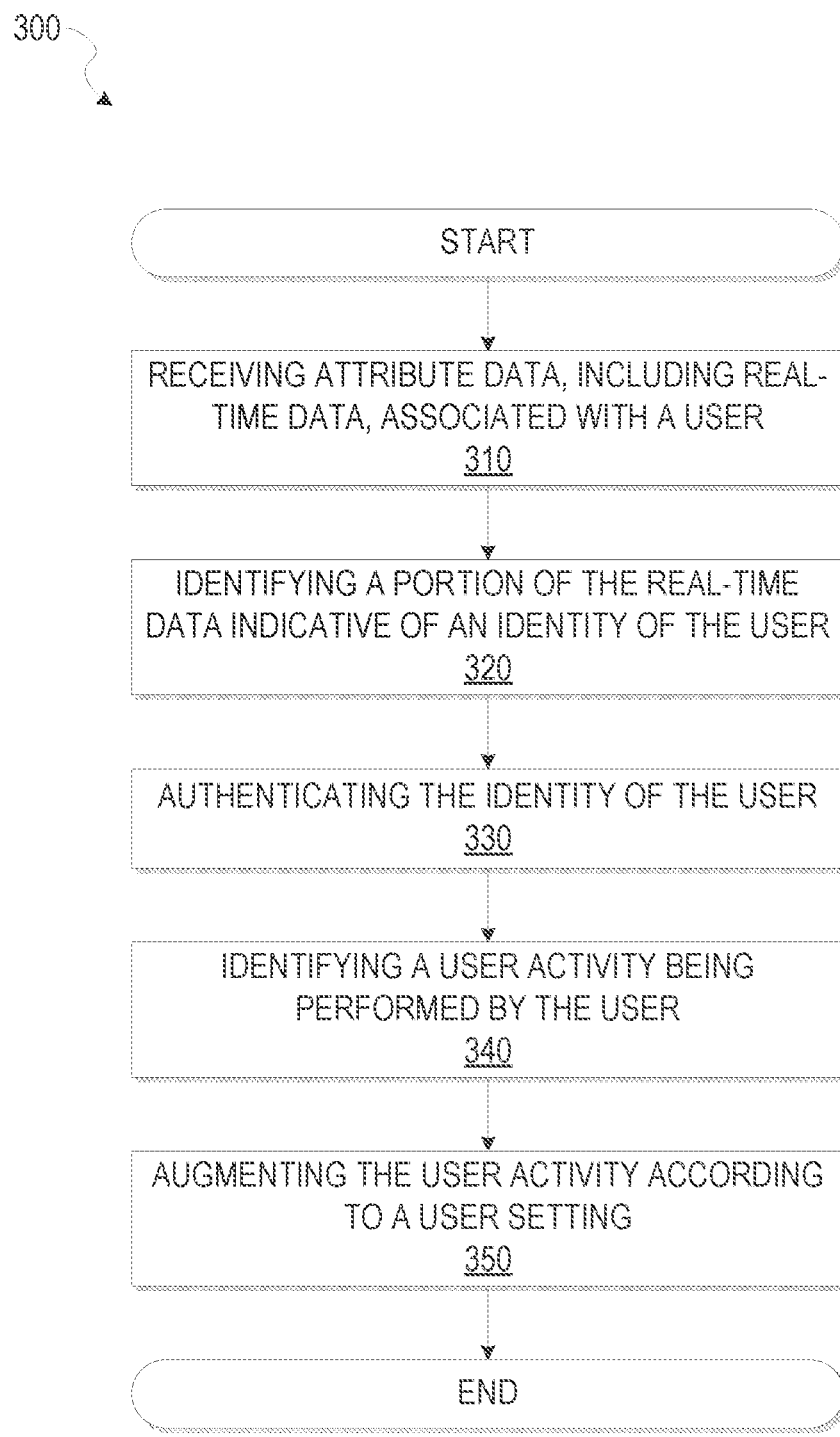
FIG. 3 is a flow diagram illustrating an example method for authenticating a user and augmenting a user activity, according to some example embodiments.

FIG. 3 is a flow diagram illustrating an example method 300 for authenticating the user and augmenting the user activity, according to some example embodiments. The operations of the method 300 may be performed by components of the data mesh system 150 and the augmentation system 152. At operation 310, the attribute module 220 may receive the attribute data associated with the user from a plurality of attribute sources. In various example embodiments, at least a portion of the attribute data may include real-time data or near real-time data. The term "real-time data," as used herein, is intended to include data associated with an event currently happening. For example, the real-time data may include user input data or sensor data communicated to the attribute module 220 after a delay interval (e.g., due to transmission delay or other delays such as being temporarily stored at an intermediate device) between capturing the data and the attribute module 220 receiving the data.

As will be discussed in connection with FIGS. 15 and 16, the attribute data may be received from a broad spectrum of attribute sources (e.g., devices, sensors, servers, databases, and other sources). Additionally, the attribute module 220 may receive the attribute data via many pathways resulting from an assortment of configurations of the attribute sources as further discussed in connection with FIGS. 14A and 14B. In an example embodiment, the attribute module 220 may receive the attribute data directly from the attribute sources. In other example embodiments, the attribute module 220 may receive the attribute data from a central device that receives attribute data from a plurality of user devices. In still other example embodiments, various user devices may be communicatively coupled in a decentralized device-to-device mesh, and the attribute module 220 may receive the attribute data corresponding to a particular device in the mesh from any of the devices in the mesh. The attribute module 220 may receive the attribute data from the attribute sources in many other configurations including various suitable combinations of configurations.

In various example embodiments, the attribute module 220 may store the attribute data in association with the user (e.g., indexed based on a user identifier) for subsequent analysis. The attribute module 220 may store the attribute data in a storage device such as the database(s) 126, for example. The attribute module 220 may access the stored attribute data using a variety of search or find schemes. For instance, the attribute data associated with a particular user may be accessed using a user identifier that corresponds to the particular user. It will be noted that the collective, aggregated attribute data may be referred to as a "data mesh."

At operation 320, the authentication module 250 may identify a portion of the real-time data indicative of an identity of the user. The attribute data including the real-time data may comprise a vast amount of data associated with the user. All or various portions (e.g., segments or pieces) of the real-time data may be indicative of the identity of the user. The authentication module 250 may identify, extract, parse, or otherwise obtain data from the real-time data that is pertinent, relevant, or otherwise useful in authenticating the identity of the user.

In an example embodiment, various devices that provide the real-time data to the attribute module 220 may correspond to the user. For instance, one or more user devices (e.g., mobile device, wearable device) may provide at least a portion of the real-time data. The user devices and the real-time data provided by the user device may be identified via a device identifier such as an Internet Protocol (IP) address, a Media Access Control (MAC) address, other unique identifies, an International Mobile Station Equipment Identity (IMEI), a Mobile Equipment Identifier (MEID), and so forth. In various example embodiments, the authentication module 250 may identify portions of the real-time data indicative of the identity of the user by matching device identifiers corresponding to the user with respective device identifiers associated with the real-time data. In a specific example, location data (e.g., as determined by a GPS component of a mobile device) may be identified by the authentication module 250 as indicative of the identity of the user if the location data originated from a device having a device identifier corresponding to the user (e.g., the location data originated from the user's mobile device). To be clear, data that originates from a device corresponding to the user may merely be indicative of the identity of the user rather than identify the user as another user may be operating the device. The identity of the user may be authenticated with respect to the real-time data in subsequent operations discussed below.

In various example embodiments, the attribute data and the real-time data may include sensor data. In an example embodiment, the authentication module 250 may identify portions of the sensor data that may be indicative of the identity of the user. For instance, the sensor data may include biometric data such as a fingerprint scan, vocal sample, electroencephalogram, or retinal scan (refer to FIG. 16 for additional sensor data). In this instance, the authentication module 250 may identify the biometric data as being indicative of the identity of the user (e.g., matching fingerprints included in the sensor data with fingerprints of the user or matching another sensor signature with a sensor signature of the user). In these particular example embodiments and the following example embodiments, the real-time data need not necessarily have originated from a device corresponding to the user.

In further example embodiments, the authentication module 250 may identify portions of the attribute data indicative of the identity of the user based on various analyses or patterns. For example, a particular device may provide location data (e.g., as determined by a GPS component of a mobile device). The authentication module 250 may determine that the location data may be indicative of the user identity based on past location data of the user. In a specific example, if the user has, in the past, exhibited a particular pattern of travel or has frequently visited a particular location (e.g., a particular route home, or spending a particular amount of time in certain locations) then the authentication module 250 may identify the real-time data corresponding to the particular device providing the location data as indicative of the user identity.

In still further example embodiments, the authentication module 250 may employ many other analyses to identify the attribute data indicative of the identity of the user. For example, the user may be a member of various websites (e.g., e-commerce websites, social website.). If the user logs into a particular website using a particular device, the authentication module 250 may identify the particular device and the attribute data received from the particular device as indicative of the user identity.

At operation 330, the authentication module 250 may authenticate the identity of the user with respect to the real-time data by analyzing the identified portion of the real-time data and the attribute data. In some example embodiments, authenticating the identity of the user with respect to the real-time data may establish that the real-time data resulted from an action of the user. For instance, if the authentication module 250 authenticates the identity of the user with respect to location data included in the real-time data, the location data may indicate the current location of the user. The authentication module 250 may analyze many different portions of the attribute data using a variety of analysis schemes and techniques to authenticate the identity of the user. The following discussion merely provides non-limiting examples of the authentication module 250 authenticating the identity of the user based on the attribute data.

In an example embodiment, the authentication module 250 may identify a portable device (e.g., mobile device, wearable device) corresponding to the user from the real-time data, and use the identified portable device as a basis for authenticating the identity of the user with respect to the real-time data. For example, the authentication module 250 may calculate the identity likelihood metric based on the identified portable device. The identity likelihood metric may indicate the likelihood that the identified portion of the attribute data identifies the user. In a specific example, the user may be operating a computer, carrying a mobile device, and wearing a smart watch. In this example, the attribute module 220 may receive the real-time data from each of the devices. If the authentication module 250 determines that the mobile device and the smart watch correspond to the user (e.g., by matching respective device identifiers with device identifiers corresponding to the user), then the authentication module 250 may authenticate the identity of the user with respect to the real-time data received from those devices. The reasoning being that if a person is determined to be carrying one or more devices belonging to the user, the person may be the user (e.g., the identified portable devices implicate or suggest the person may be the user). The more devices of the user that the person may be carrying, the stronger the basis may be that the person is the user.

In continuing with the above example, the authentication module 250 may authenticate the identity of the user with respect to the real-time data corresponding to the computer based on the authentication with respect to the mobile device and wearable device. The authentication module 250 may perform this authentication, for example, based on the location of the computer relative to the location of the portable devices of the user. For example, if the location of the computer is the same or within a short distance (e.g., an arms length) of the location of the portable devices of the user, the authentication module 250 may infer that the user is using the computer. The location of the computer may be established based on sensor data included in the real-time data such as near field, Bluetooth®, or other interactions between the portable devices and the computer. In other words, the location of a particular portable device may be known based on a GPS component of the particular portable device, and the location of a device in communication with the particular portable device may be inferred based on short-range communications that operate over short distances. Thus, in this example, the authentication module 250 may authenticate the identity of the user with respect to the real-time data received from the computer. The above is merely a non-limiting example and many other techniques may be employed by the authentication module 250 to authenticate the identity of the user with respect to the real-time data of various devices.

In further example embodiments, the authentication module 250 may use other indications of the identity of the user to authenticate the identity of the user with respect to the real-time data. For example, the authentication module 250 may use sensor data, at least in part, to authenticate the identity of the user. For instance, the sensor data may include biometric data that the authentication module 250 may use to authenticate the identity of the user. In a specific example, the biometric data may include biometric identification data such as fingerprint scans, vocal samples, retinal scans, facial scans, or electroencephalogram data (see FIG. 16 for additional biometric identification data). The authentication module 250 may match, correlate, or otherwise determine that the biometric data corresponds to the user to authenticate the identity of the user with respect to the real-time data.

In still further example embodiments, the authentication module 250 may use location data to authenticate the identity of the user with respect to the real-time data. For example, the location data (e.g., as determined by a GPS component of a mobile device) may indicate a location pattern that the authentication module 250 may use to authenticate the identity of the user. In this example, the location pattern may comprise being at a particular location at a particular time or a particular route at a particular time. In a specific example, the location data may indicate a location that may be the home of the user. Given that the location may be the home of the user, it may be probable that the real-time data provided by the mobile device may correspond to the user. Thus, in some example embodiments, the authentication module 250 may authenticate the identity of the user with respect to the real-time data based on a location corresponding to the real-time data that may be indicative of the user (e.g., a location that may be typically access restricted for which the user has access such as a home or office).

Figure 4:
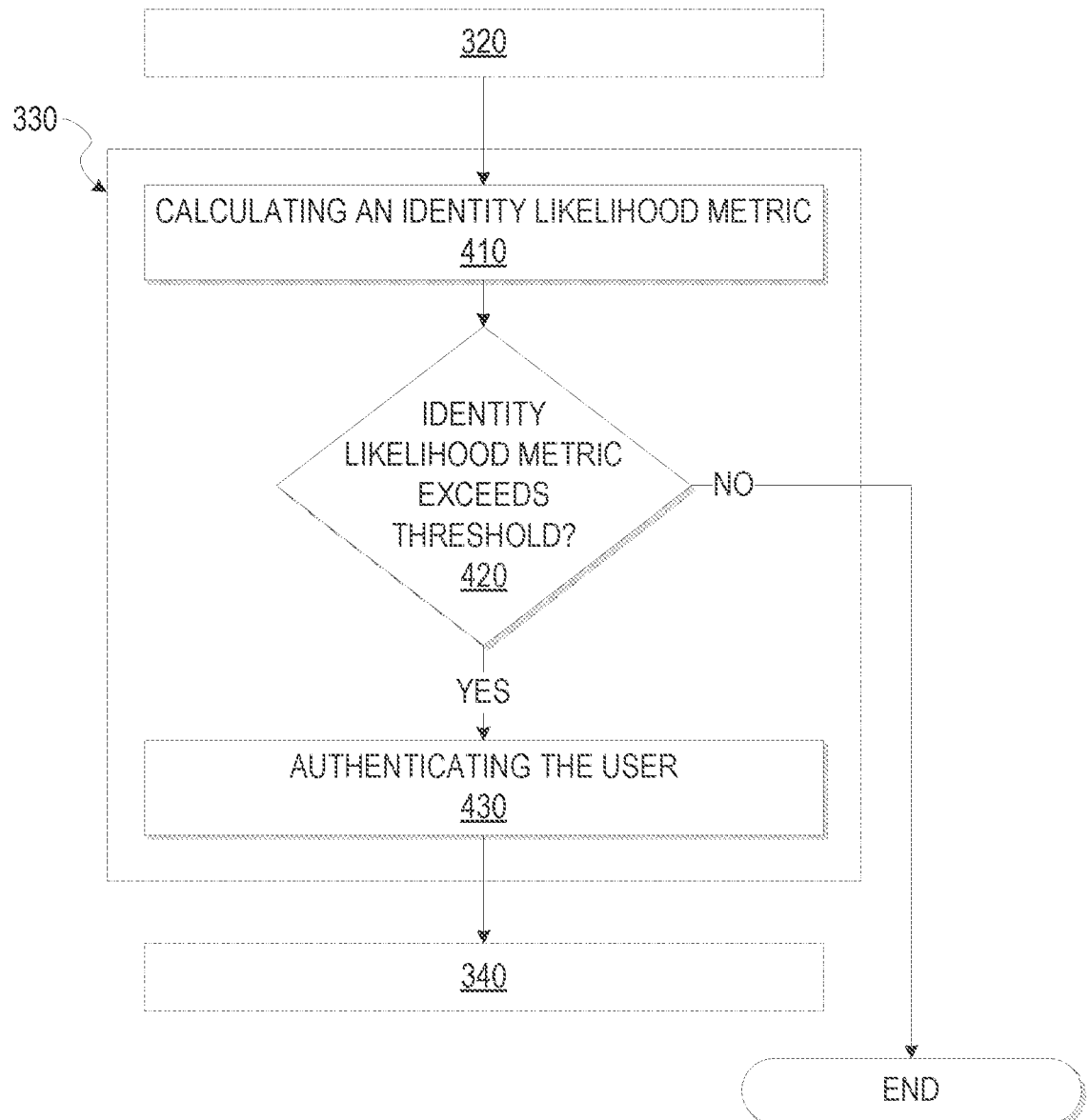
FIGS. 4 and 5 are flow diagrams illustrating further example operations of the method of FIG. 3, according to some example embodiments.

In continuing with the discussion of the operation 330, FIG. 4 is a flow diagram illustrating further example operations of the method 300 of FIG. 3, according to some example embodiments. As described above, subsequent to the operation 320, at the operation 330, the authentication module 250 may authenticate the identity of the user by analyzing the identified portion of the real-time data. In addition, at operation 410, the authentication module 250 may calculate the identity likelihood metric based on the identified portion of the attribute data. The identity likelihood metric may indicate the likelihood that the identified portion of the attribute data identifies the user (e.g., the probability that the identified portion of the real-time data identifies the user).

The authentication module 250 may calculate the identity likelihood metric using a variety of schemes and techniques. In an example embodiment, the authentication module 250 may weight various portions of the real-time data indicative of the identity of the user. For example, the authentication module 250 may more heavily weight the real-time data that strongly indicates the identity of the user (e.g., a fingerprint scan that matches a fingerprint scan of the user). Conversely, the authentication module 250 may weight less heavily the real-time data that does not strongly indicate the identity of the user (e.g., real-time data indicating a user device in a particular location at a particular time may be indicative of the identity of the user but may not as strongly implicate the identity of the user as biometric identification data). In some example embodiments, the authentication module 250 may use a combination of the real-time data to calculate the identity likelihood metric.

Subsequent to calculating the identity likelihood metric, at decision 420, the authentication module 250 may determine whether the identity likelihood metric exceeds an authentication threshold. In an example embodiment, when the identity likelihood metric exceeds the authentication threshold, the authentication module 250 may authenticate the identity of the user. Conversely, if the identity likelihood metric does not exceed the threshold, the authentication module 250 may not authenticate the identity of the user, and no further operations may be performed in method 300.

At operation 430, the authentication module 250 may authenticate the identity of the user. As discussed above, the authentication module 250 may use the identity likelihood metric exceeding the authentication threshold as a factor in authenticating the identity of the user with respect to the real-time data. The authentication module 250 may use the identity likelihood metric alone or in conjunction with other factors to authenticate the identity of the user. Once the identity of the user is authenticated with respect to the real-time data, subsequent operations of the method 300 may be performed.

Figure 5:
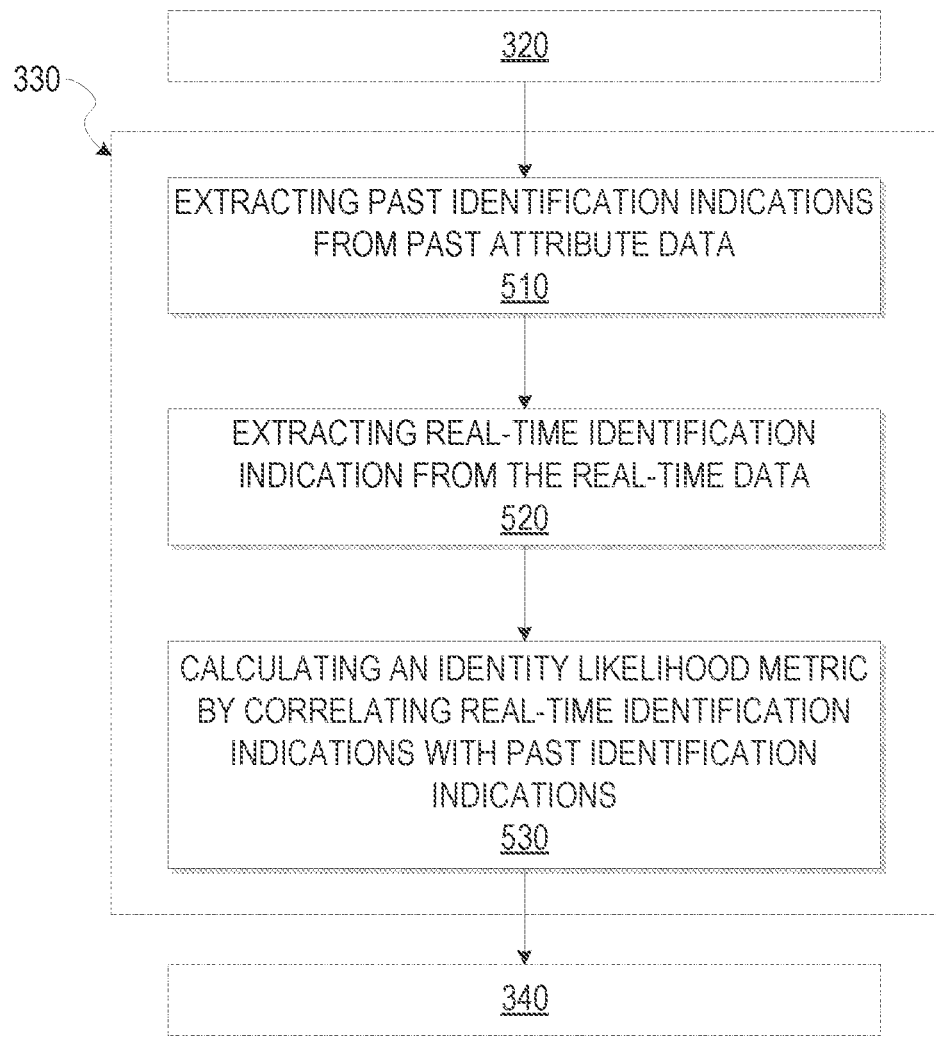

In further discussing the operation 330, FIG. 5 is a flow diagram illustrating a further embodiment for authenticating the identity of the user, according to some example embodiments. Subsequent to the operation 320, at the operation 330, the authentication module 250 may authenticate the identity of the user by analyzing the identified portion of the attribute data. In addition, at operation 510, the authentication module 250 may derive, extract, or otherwise obtain past identification indications from past attribute data. For example, if the past attribute data includes location data, the authentication module 250 may extract favorite or frequent locations corresponding to the user.

At operation 520, the authentication module 250 may derive, extract or otherwise obtain real-time identification indications from the real-time data. For instance, the real-time data may include location data. In some example embodiments, the real-time identification indications may be derived. For example, the authentication module 250 may derive location information based on short-range communications with devices of a known or fixed location.

At operation 530, the authentication module 250 may calculate the identity likelihood metric by correlating, matching, or otherwise comparing the real-time identification indications with the past identification indications. For example, if the real-time data indicates a particular location, the authentication module 250 may match the particular location with a frequent location of the user to authenticate the identity of the user. Although the discussion of FIG. 5 is mostly directed to location data, the authentication module 250 may, in a similar manner, use many other types of data included in the attribute data to calculate the identity likelihood metric.

Referring back to FIG. 3, at operation 340, the activity module 255 may identify or infer a user activity being performed by the user based on the real-time data. In other words, the activity module 255 may identify a user objective (e.g., logging into a website) being advanced by the user based on the real-time data. The user activity may include a wide variety of activities such as, for example, operating a computer (e.g., logging into a website), jogging in the park, walking toward the refrigerator, and streaming video or other media content. In an example embodiment, the activity module 255 may identify the user activity based on sensor data and status data received from one or more user devices. The status data may indicate activity associated with a particular device. For example, the user devices may include a mobile device that provides location data and a variety of other user devices that may provide the status data (e.g., a smart TV that indicates current operating status such as streaming a particular piece of media). In this example, the activity module 255 may infer the user activity by analyzing the location data in conjunction with the status data (e.g., the user may be proximate to the smart TV based on the location data and the smart TV may indicate that it is streaming a video).

In another example, the activity module 255 may infer, extract, or derive the status data for a particular device based on an analysis of sensor data corresponding to the particular device. For example, a mobile device may be equipped with accelerometers that measure motion and provide motion data. If the motion data indicates that the device is not moving, the activity module 255 may infer that a person may not be carrying the particular device. In this scenario, the activity module 255 may not infer the user activity based on a device that is not currently being carried by the user. The above examples are merely non-limiting examples of the activity module 255 identifying or inferring the user activity based on the real-time data. The activity module 255 may use many other portions of the real-time data in a variety of schemes to identify or infer the user activity. At operation 350, the activity module 255 may augment, adapt, or otherwise modify the user activity according to a user setting or user preference. In other words, the activity module 255 may augment an environment of the user based on a user preference to facilitate the user's advancement towards the user objective. The environment of the user is intended to include, for example, user devices within the vicinity of the user. For example, if the user activity includes an authorization task (e.g., logging into a website), the activity module 255 may augment the user activity by adjusting a security level of the authorization task. In some example embodiments, the activity module 255 may adjust the security level of the authorization task based on the identity likelihood metric. For example, if the identity likelihood metric indicates strongly that the identity of the user is authenticated, then the security level may be reduced more than if the identity likelihood metric did not strongly indicate the identity of the user is authenticated. In some example embodiments, adjusting the security level of the authorization task may include automatically performing the authorization task on behalf of the user. For example, if the authentication module 250 has authenticated the identity of the user and the user activity includes accessing a particular website, then the activity module 255 may automatically log the user into the particular website.

In a further specific example, the identified user activity may comprise making a payment (e.g., an electronic payment to an e-commerce website corresponding to an item listing listed on the e-commerce website or a electronic payment to a merchant at a physical store). The activity module 255 may augment the user activity associated with making a particular payment by facilitating the payment between the user and the payee. For instance, based on the authentication of the identity of the user, the user may not need to provide security credential or provide fewer security credentials to make the payment.

Figure 6:
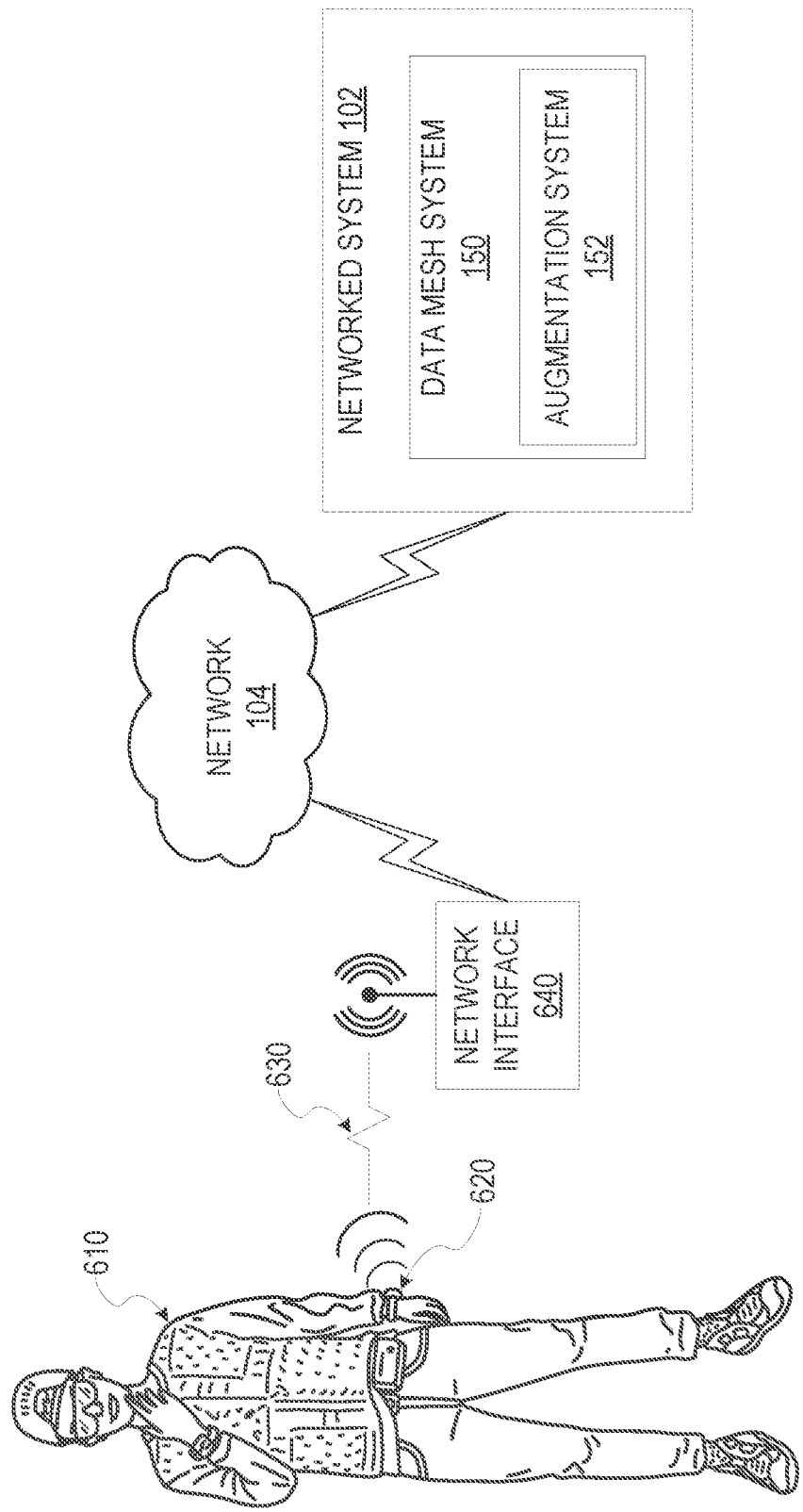
FIG. 6 depicts communication between a device of the user and the data mesh system, according to some example embodiments.

To assist in illustrating the above discussion, FIG. 6 depicts communication between a device of the user and the data mesh system 150, according to some example embodiments. In the illustration of FIG. 6, a user 610 may be wearing one or more smart devices such as a smart watch 620. The smart watch 620 may be communicatively coupled to the network 104 via various modalities. For example, the smart watch 620 may be communicatively coupled to a network interface 640, which, in turn, is communicatively coupled to the network 104. For instance, the smart watch 620 may send signals 630 that are received at the network interface 640. In another example, the smart watch 620 may be communicatively coupled to the network 104 without the network interface 640. In addition, the networked system 102, including the data mesh system 150 and the augmentation system 152, may be communicatively coupled to the network 104.

Thus, the smart watch 620 of the user 610 may be communicatively coupled to the data mesh system 150 including the augmentation system 152. The data mesh system 150, including the augmentation system 152, may receive or access the attribute data corresponding to the smart watch 620 via the network 104. Similarly, the data mesh system 150, including the augmentation system 152, may communicate or exchange data with the smart watch 620 to facilitate augmentation of the user activity such as communicating instructions to present a user interface. Although the example of FIG. 6 depicts an example smart watch, it will be appreciated that a wide variety of other devices may similarly be configured to interact with the data mesh system 150.

FIGS. 7-10 are flow diagrams illustrating further example operations of the method 300 of FIG. 3, according to some example embodiments. Subsequent to the operation 340, at the operation 350, the activity module 255 may augment the user activity according to the user setting. Each of the flow diagrams of FIGS. 7-10 illustrates additional operations of the operation 350. The additional operations of the operation 350 include various example embodiments of augmenting the user activity according to the user setting. The following discussion merely describes non-limiting examples and many other schemes and techniques may be employed by the augmentation system 152 to augment the user activity using the user setting.

In the flow diagram of FIG. 7, subsequent to the operation 340, the settings module 260 may determine the user setting based on the attribute data and the user activity at operation 710. For example, the settings module 260 may store a plurality of user settings in a storage device such as the database(s) 126. Subsequent to determining the user activity, the settings module 260 may determine the user setting associated with or pertaining to the user activity. For instance, the user activity may include the user streaming a movie to a particular user device. Based on the activity module 255 identifying the activity of streaming the movie, the settings module 260 may determine the user setting associated with augmenting the user activity of streaming the movie such as, for example, automatically pausing the streaming when the user leaves a vicinity of the particular user device presenting the movie to the user.

At operation 720, the activity module 255 may augment the user activity according to the determined user setting. In continuing with the example above, the user activity may include streaming the movie. The activity module 255 may augment the user activity according to the determined user setting. For example, the activity module 255 may automatically pause or otherwise halt the movie based on a trigger (e.g., the user leaving the vicinity or answering a phone call), present the streaming movie to another display based on the user setting and a location of the user, and so on. Although the above discussion is directed to streaming the movie, the activity module 255 may augment the user activity that includes many other activities and based on many different types or kinds of user settings.

In the flow diagram of FIG. 8, subsequent to the operation 340, the characteristic module 225 may infer or measure directly user characteristics based on an analysis of at least a portion of the attribute data at operation 810. In some example embodiments, the characteristic module 225 may store the inferred user characteristics for subsequent analysis, for example, in a storage device such as database(s) 126. The characteristic module 225 may infer a vast spectrum of the user characteristics from the attribute data. A few specific examples of user characteristics may include demographic data (e.g., age, gender, marital status, number of children), user preferences (e.g., being a morning person, favorite locations, enjoying spicy food), idiosyncrasy (e.g., being forgetful, such as draining the battery on a mobile device; or being impatient, such as a line breaker that will leave a store if the line is too long), qualities (e.g., being athletic, being tall, having a large vocabulary), personality traits (e.g., being a risk taker), actions, activities (e.g., working for a non-profit), attitudes, habits (e.g., being a coffee drinker), behaviors, beliefs, biases, demeanor, and physical characteristics of the user (e.g., height, weight, garment sizes, eye color, hair color). The specificity of the characteristics may range from very narrow (e.g., drinks a particular brand of soda) to very broad (e.g., being generally philanthropic). To illustrate inferring the user characteristic from the attribute data, the attribute data may include user location data that may indicate frequent visits to a local school, local soccer fields, and the like. In this example, the characteristic module 225 may infer that the user has children based on the types of locations the user may be frequently visiting.

In some instances, the characteristic module 225 may perform varying degrees of inferential analysis of the attribute data to derive the user characteristics. For example, the characteristic module 225 may infer the user's wake-up time based on user device activity or other activity (e.g., connected alarm clock settings, logins to accounts, and various other user activities that may indicate a wake-up time). In this example, the characteristic module 225 may infer a particular user characteristic that may be of a larger inferential jump such as the user being a morning person or a person that likes to sleep in. The degree of inferential jump may be configurable. In some example embodiments, the characteristic module 225 may employ various techniques to minimize or otherwise control incorrect inferences (e.g., machine learning, other learning algorithms).

In further example embodiments, the characteristic module 225 may learn or evolve as more of the attribute data is received (e.g., via machine learning techniques or other learning algorithms). For example, the attribute data may include location data of the user. The characteristic module 225 may infer a favorite location of the user based on a pattern (e.g., frequently visited locations) in the location data. However, the characteristic module 225 may subsequently receive employment data of the user that may indicate a current employer including an employer location. The characteristic module 225 may learn, update, or otherwise adapt to account for the new attribute data. Thus, in this example, the characteristic module 225 may not infer a favorite location of the user if the location is a work location of the user. In some instance, the user may provide input directly (e.g., via a user interface configured to receive inferential guidance from the user) to facilitate the characteristic module 225 in inferring characteristics from the attribute data (e.g., user input indicating that a particular inferred characteristic is incorrect or providing input to be used as a basis for future inferences).

In other instances, the characteristic module 225 may perform very little or no analysis to derive the user characteristic from the attribute data. For example, the attribute data may include an alarm time setting from a connected alarm clock (e.g., a smart phone with an alarm clock app). The alarm time setting may directly indicate a wake-up time. Since the attribute data directly relates to a particular user characteristic, the characteristic module 225 need not perform analysis to derive the user characteristic.

In some example embodiments, the user characteristic may comprise predefined characteristics or dynamically determined characteristics. For instance, a particular set of characteristics may be predefined (e.g., work location, home location, marital status, socio-economic level). The characteristic module 225 may determine that particular predefined characteristics are associated with the user based on an analysis of the attribute data. In other instances, the characteristic module 225 may dynamically determine characteristics based on the attribute data. For example, the attribute data may indicate that the user owns a particular exotic pet. Although there may not be a predefined characteristic associated with the particular exotic pet, the characteristic module 225 may determine the user characteristic of owning an exotic pet from the attribute data.

At operation 820, the settings module 260 may determine the user setting based on the inferred user characteristics and the user activity. For example, the inferred user characteristics may indicate the user has an affinity to view user interfaces on a largest screen available. In this example, the settings module 260 may determine that the user setting includes presenting user interfaces to the largest screen available.

In further example embodiments, the settings module 260 may identify similar users to the user based on the attribute data or the user characteristics. For instance, the settings module 260 may identify users associated with the same or similar demographic data as that of the user. In an example embodiment, the settings module 260 may determine the user setting based on attribute data or characteristics corresponding to the similar users. For example, the settings module 260 may access the user characteristics corresponding to other users and correlate, match, or otherwise compare the user characteristics of the user with the user characteristics of other users to identify the similar users.

At operation 830, the activity module 255 may augment the user activity according to the determined user setting. For example, if the user is viewing a particular user interface on a mobile device and the user is within a distance of a larger screen, such as a computer or smart TV, the activity module 255 may augment the user activity by presenting the particular user interface on the larger screen.

In the flow diagram of FIG. 9, subsequent to the operation 340, the activity module 255 may determine that the user activity includes a presentation of a user interface to the user at operation 910. For example, the presentation of the user interface may include the user viewing a movie, using a website, or reading an email. The activity module 255 may determine that the user activity includes the presentation of the user interface based on the real-time data. For instance, the status data of a particular device of the user may indicate that the particular device may be presenting the user interface to the user.

At operation 920, the activity module 255 may identify presentation devices available to the user based on the attribute data that are capable of presenting the user interface to the user. For instance, the user may be in a room that includes several user devices such as a smart TV, a laptop computer, and a mobile device. The activity module 255 may identify these devices based on the real-time data. For example, if the smart TV is active and connected to a network, the activity module 255 may query the smart TV to determine whether it may be capable of presenting the user interface.

At operation 930, the activity module 255 may determine an alternate presentation device from among the identified presentation devices based on the user setting. The activity module 255 may determine the alternate presentation device based on a number of factors. For example, the user setting may indicate the user has an affinity to view a larger screen when available. Based on this user setting, the activity module 255 may identify a presentation device with a larger display. In another example, the activity module 255 may determine that the alternate presentation device should be within a close vicinity of the user. For example, a particular presentation device that is out of view of the user may not be the best choice for the alternate presentation device. The activity module 255 may make this determination based on location data included in the real-time data. In still another example, the activity module 255 may identity a presentation device that is portable. For example, the activity module 255 may determine that the user is viewing a movie and that the user is leaving the vicinity, and may determine that a portable device to continue playing the movie is a desirable choice for the alternate presentation device.

At operation 940, the activity module 255 may cause presentation of the user interface to the user with the alternate presentation device. In a specific example, the user may be viewing a live sporting event on a smart TV. When the user leaves the vicinity of the smart TV, the activity module 255 may cause presentation of the live sporting event to the alternate presentation device such as another smart TV that is viewable to the user or a portable device of the user to allow the user to continue view the live sporting event despite being out of view of the initial presentation device.

In the flow diagram of FIG. 10, subsequent to the operation 340, the activity module 255 or the characteristic module 225 may determine a current location of the user based on the real-time data at operation 1010. For example, the real-time data may include location data as determined by a GPS component of a mobile device, near field beacon detections, and other location services.

At operation 1020, the activity module 255 or the characteristic module 225 may access device location data included in the attribute data that includes the real-time data. Similar to the operation 1010, the activity module 255 may access, receive, or otherwise obtain the device location data based on GPS, near field beacon detections, and other location services. Although FIG. 10 illustrates performing the operation 1010 prior to operation 1020, in alternative example embodiments, the operation 1010 may be performed concurrently or after the operation 1020. For instance, the current location of the user and the device location data may be received, access, retrieved, derived, or otherwise obtained by the activity module 255 at the same time in in any order and the subsequent operations illustrated in FIG. 10 performed.

At operation 1030, the activity module 255 may identify user devices within an operation distance of the user based on the current location of the user and the device location data. The operation distance may be configurable or dynamically determined. In some example embodiments, the operation distance may vary from device to device. For example, the operation distance corresponding to a smart TV may be a reasonable distance such that the user may view the smart TV. In other examples, the operation distance corresponding to a mobile device may be a reasonable distance (e.g., arm's length) such that he user may touch of the mobile device.

At operation 1040, the activity module 255 may augment the operation of the identified user devices according to the user setting. In some example embodiments, the activity module 255 may augment the operation of the identified user device according to the user setting and the user activity. For example, if the user activity includes the user moving into a smart kitchen, the user activity module 255 may augment the operation of various user devices according to the user setting based on moving into the smart kitchen. For instance, relevant notifications may be pushed to a mobile device of the user based on the user moving into or being in the smart kitchen (e.g., a notification regarding the status of a smart kitchen appliance). In another instance, the activity module 255 may cause the smart appliance of the smart kitchen to perform a task on behalf of the user automatically based on the user moving into the smart kitchen (e.g., automatically brew a cup of coffee).

Figure 11:
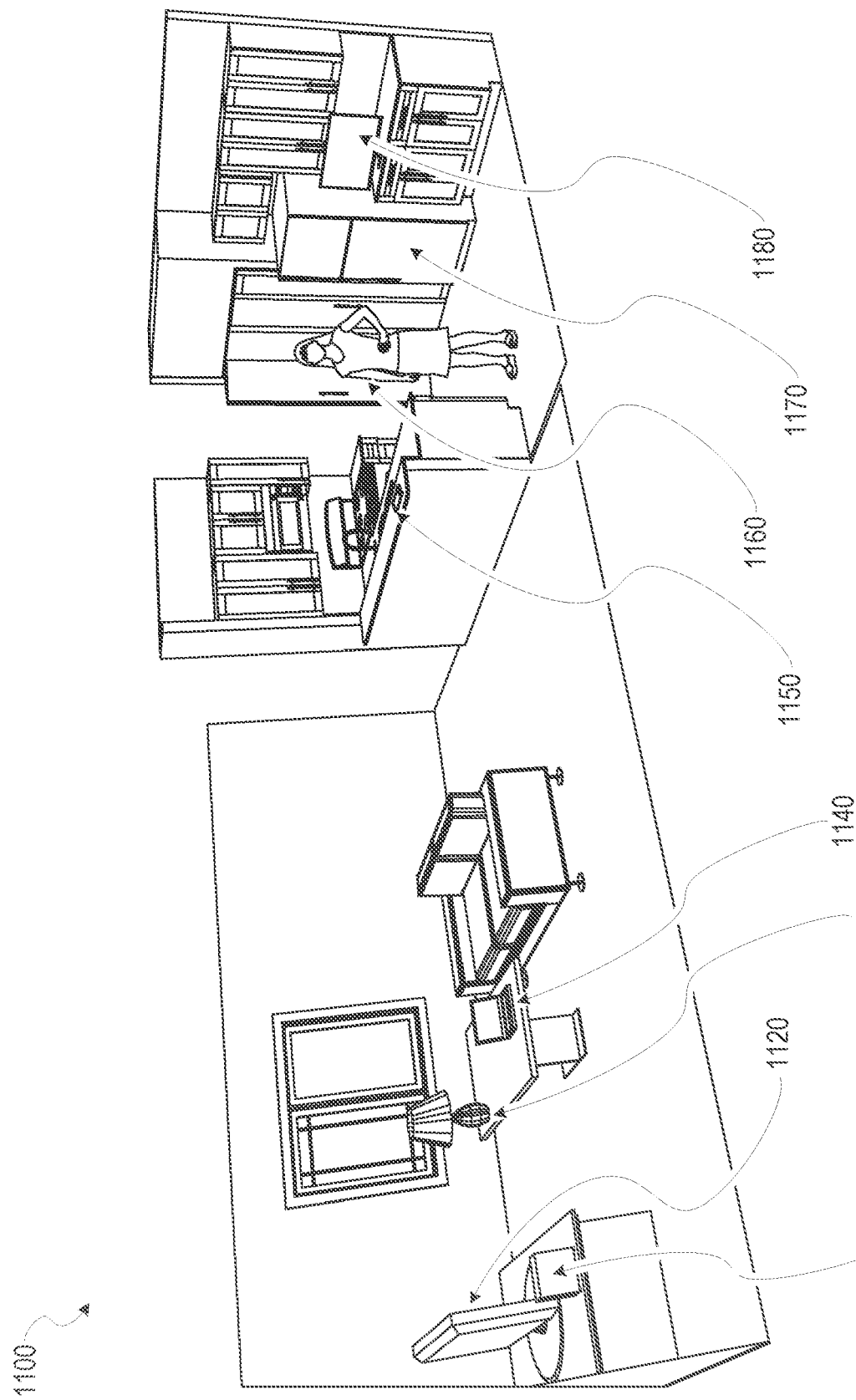
FIG. 11 illustrates augmenting an example user activity, according to some example embodiments.

To help illustrate the concepts described above, FIG. 11 illustrates non-limiting examples of augmenting the user activity, according to some example embodiment. A scene 1100 depicts a living room attached to an open kitchen. The scene 1100 may include a media entertainment device 1110, a smart TV 1120, a lamp 1130, a mobile computer 1140, a mobile device 1150, a user 1160, a smart refrigerator 1170, and a kitchen display 1180. Each of the devices 1110-1150, 1170, and 1180 may be attribute sources coupled to a network (e.g., the network 104) and operable to communicate with the data mesh system 150. In various example embodiments, the real-time data may include location data corresponding to the user. For instance, the user 1160 may be carrying a mobile device or another smart device (e.g., smart watch, NFC enable smart ring) that may provide real-time location data (e.g., as determined by a GPS component, beacon location detect, or other location services). In this way, the location of the user 1160 may be tracked, monitored, or observed via a particular device the user is wearing or the location of the user 1160 may be derived from various real-time data associated with the user's location included in the attribute data (e.g., Bluetooth® handshakes between a device the user is wearing and a another device with a known or fixed location). The activity module 255 may infer the user activity based the real-time data and augment the user activity based on the user setting.

In an example embodiment, the activity module 255 may determine that the user 1160 may be streaming media content to the smart TV 1120 and may be moving away from the smart TV 1120 towards the kitchen. In this example, the activity module 255 may identify the mobile computer 1140 and the display 1180 as alternate presentation devices. The activity module 255 may further determine that the kitchen display 1180 may be a desirable alternate presentation device as it may be within viewing distance of the user. The activity module 255 may then augment the activity of the user by presenting the streaming media content on the kitchen display 1180 and halting the presentation to the smart TV 1120. In further example embodiments, the activity module 255 may further determine that the user 1160 has opened the smart refrigerator 1170 and may pause the streaming of the media content while the user 1160 may be using the smart refrigerator 1170.

In another example embodiment, the authentication module 250 may authentication the identity of the user 1160 by detecting a mobile device or wearable the user 1160 may be carrying in proximity to the kitchen display 1180 (e.g., detected from the attribute data that may include a data feed from the mobile device, the wearable device, and the kitchen display 1180). Subsequently, the activity module 255 may detect that the user is walking within an operating distance (e.g., a reasonable distance such as a distance that would place the user 1160 within the same room a particular device) of a particular user device such as the kitchen display 1180. The activity module 255 may detect the user 1160 within the operating distance of the kitchen display 1180 via a GPS component of a mobile device the user may be carrying, short range communication detections (e.g., Bluetooth® or near field communication handshakes between the mobile device of the user and the kitchen display 1180), and so on. The activity module 255 may then present a personalized message to the user 1160 on the kitchen display 1180 that may be pertinent or relevant to the user 1160 with respect to the context or environment of the user 1160 as determine by the settings module 260 via an analysis of the attribute data (e.g., the attribute data may include calendar information corresponding to the user 1160 or food inventory information as provided by the smart refrigerator 1170). For instance, the personalized message may be a reminder regarding an upcoming appointment or a reminder to purchase a particular product the user may be running low on. For a particular user other than the user 1160, the activity module 255 may present a different personalized message or perform a different augmentation of the user activity. Thus, in this example, the augmentation system 152 has received the attribute data associated with the user (e.g., the user 1160), authenticated the identity of the user with respect to the real-time data (e.g., detecting a portable device corresponding to the user 1160), identified the user activity (e.g., walking near the kitchen display 1180), and augmented the activity of the user according to the user setting (e.g., presenting the personalized message to the user 1160 on the kitchen display 1180).

In yet another example embodiment, the activity module 255 may detect the user may be in a vicinity of the lamp 1130 (e.g., the user 1160 in the same room as the lamp 1130) via location tracking of the user 1160 (e.g., a wearable device on the user's person). In response to the activity module 255 detecting the user 1160 near the lamp 1130, the activity module 255 may augment the environment of the user by switching on the lamp or changing a brightness of the lamp (e.g., the lamp 1130 may be a smart lamp operable to execute various commands or the lamp 1130 may be coupled to a smart outlet operable to control various functions of the lamp 1130). The activity module 255 may adjust the operation of the lamp 1130 according to the user setting corresponding to the lamp 1130 as determined by the settings module 260 (e.g., adjusting the brightness of the lamp according to historical brightness of the lamp corresponding to the user).

Figure 12:
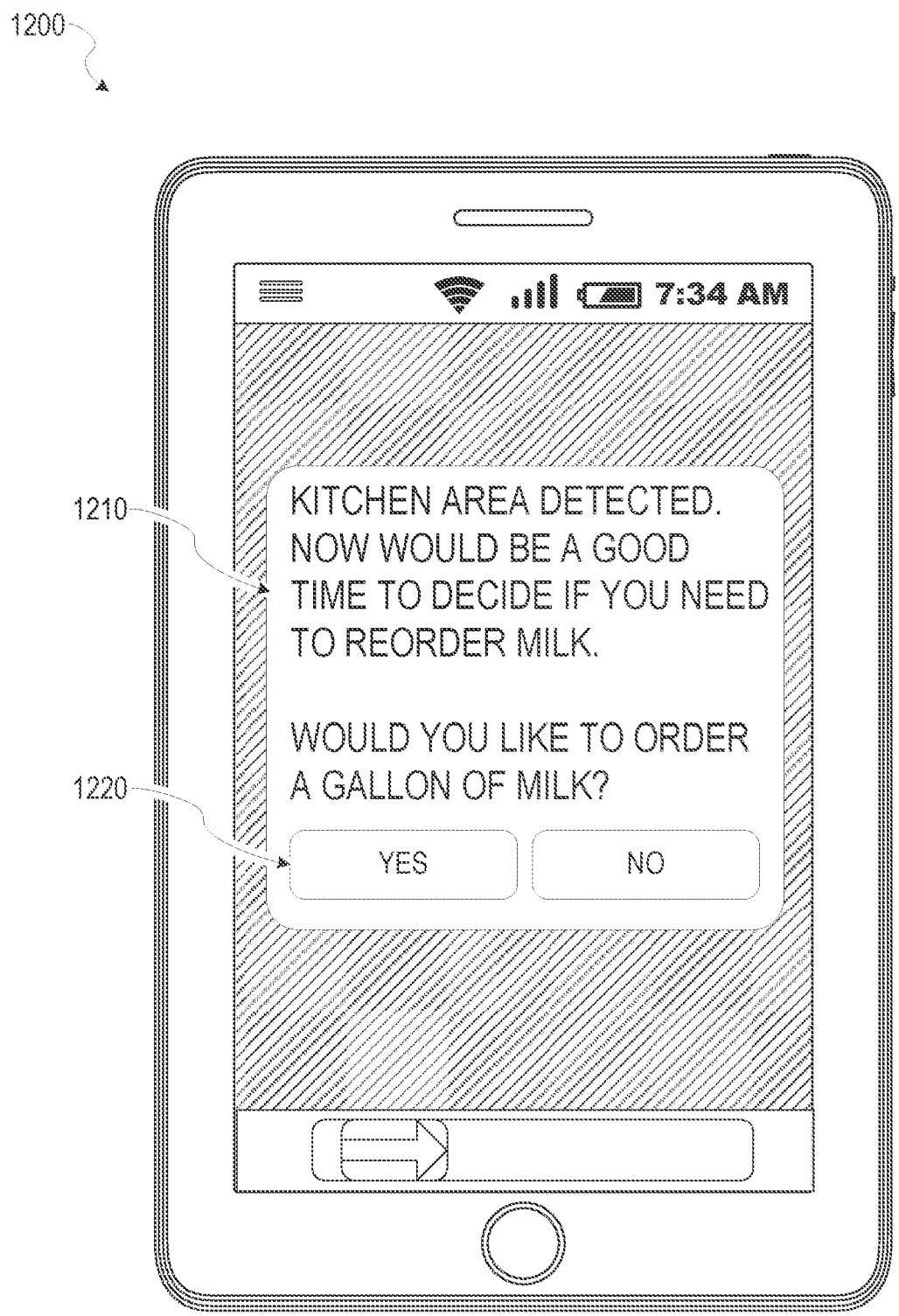
FIG. 12 depicts an example user interface to facilitate augmentation of a user activity, according to some example embodiments.

FIG. 12 depicts an example user interface to facilitate augmentation of a user activity, according to another embodiment. In example embodiments, the activity module 255 may identify the user activity, such as, the user moving into a particular location (e.g., the kitchen). In some embodiments, the activity module 255 may augment the activity of the user by presenting a user interface to the user. An example mobile device 1200 displays an example notification 1210 is shown. The activity module 255 may present notifications, such as the notification 1210, to the user that are relevant within the context of the user activity. For instance, if the user has just entered the kitchen, it may be a good time to provide the user with information relevant to the kitchen, such as, kitchen supplies. In an example embodiment, the attribute data may include data received from a smart refrigerator (e.g., smart refrigerator 1150) indicating a food supply. The activity module 255 may augment the activity of the user by presenting a notification to the user regarding the food supply. In this example embodiment, the user may interact with the notification using user interface elements 1220 (e.g., place an order for the item or dismiss the notification).

Figure 13:
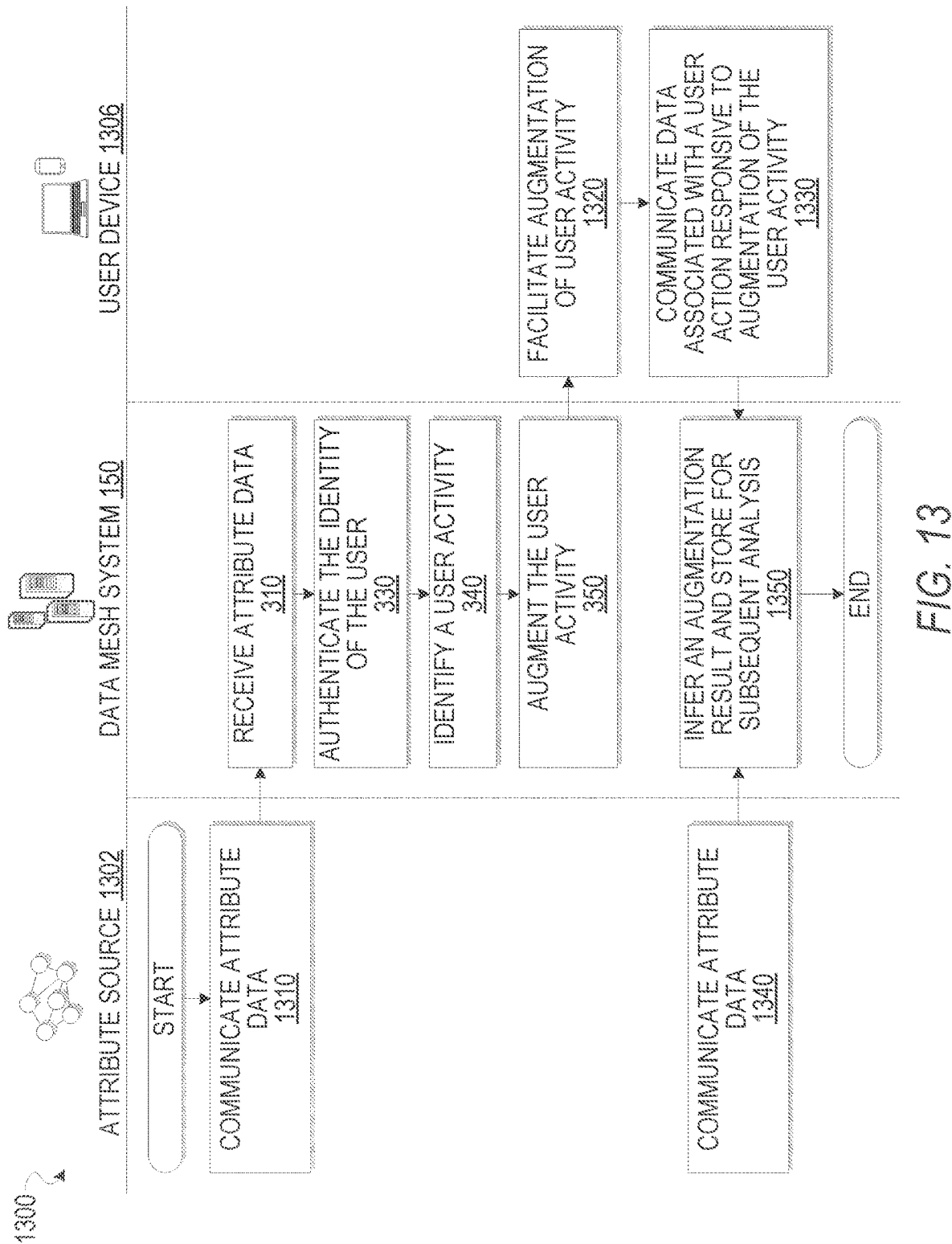
FIG. 13 is a flow diagram illustrating various communications to facilitate the method of FIG. 3, according to some example embodiments.

FIG. 13 is a flow diagram 1300 illustrating various communications to facilitate the method of FIG. 3, according to example embodiments. At operation 1310, attribute sources 1302 may communicate attribute data to the data mesh system 150. As described above with reference to FIG. 3, the data mesh system 150 may receive the attribute data at operation 310, authenticate the identity of the user at the operation 330, identify the user activity at operation 340, and augment the user activity at the operation 350.

The data mesh system 150 may augment the user activity by communicating with a user device 1306. At operation 1320, the user device 1306 may facilitate augmentation of the user activity. For instance, the data mesh system 150 may communicate instructions to the user device 1306 to present a particular user interface (e.g., a notification), and the user device 1306 may present the user interface in response.

At operation 1330, the user device 1306 may communicate data associated with a user action responsive to the user activity. The data associated with the user action responsive to the augmentation of the user activity may indicate whether the augmentation is desired by the user. For instance, if the augmentation included presenting a notification to the user and the user dismisses the notification, then the settings module 260 may use that as a basis for determining the user setting in subsequent analysis.

Similarly, at operation 1340, the attribute source 1302 may communicate attribute data associated with the user action responsive to the augmentation of the user activity. For instance, the data mesh system 150 may request, retrieve, or otherwise obtain the attribute data associate with the user action from the attribute sources 1302 responsive to the augmentation of the user. The attribute source 1302 may communicate the attribute data that indicates whether the augmentation was desired by the user.

At operation 1350, the settings module 260 may infer an augmentation result from the data received from the user device 1306 and the attribute source 1302. The settings module 260 or characteristic module 225 may identify a user action of the user based on the real-time data, the user action being in response to the augmented user activity or environment. For instance, the user action may include dismissing a notification or interacting with a user interface. The augmentation result may indicate whether the augmentation was desired by the user. For instance, the attribute data may include engagement data that indicates the user's engagement in a particular activity, such as, clicking on user interface elements. The settings module 260 may infer the augmentation result based on the engagement data or other data. In further example embodiments, the activity module 255 may store the augmentation result in a storage device such as the databases 126 to be used subsequently to determine the user setting. Thus, the settings module 260 may evolve the user settings to better fit the user over time as more data associated with augmentations is received.

Figure 14B:
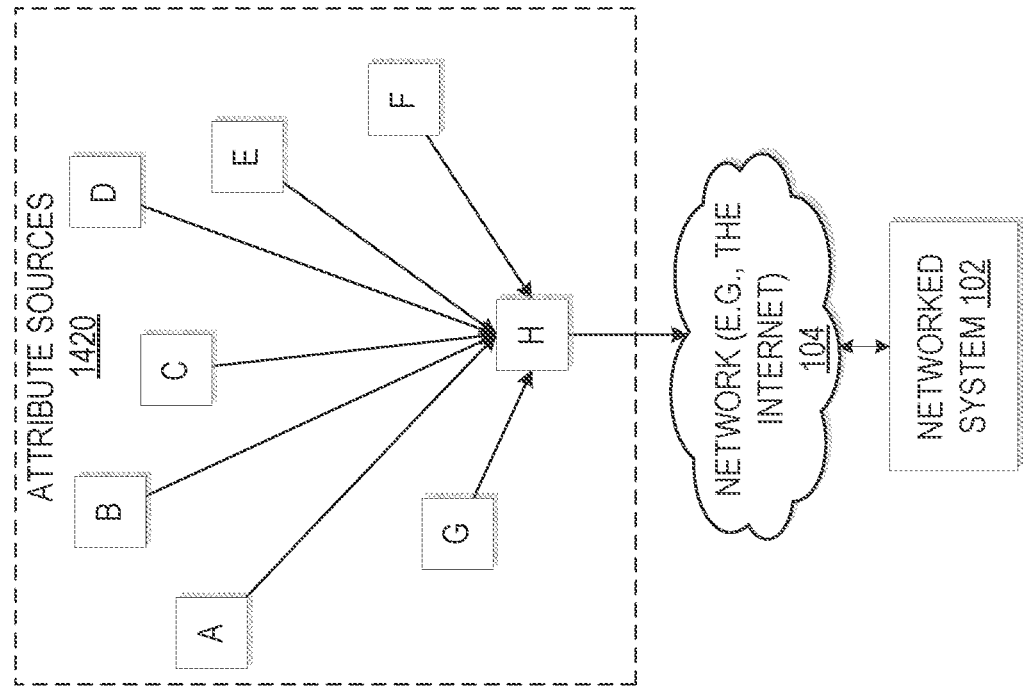
FIGS. 14A and 14B depict example configurations for communicatively coupling attribute sources, according to some example embodiments.
Figure 14A:
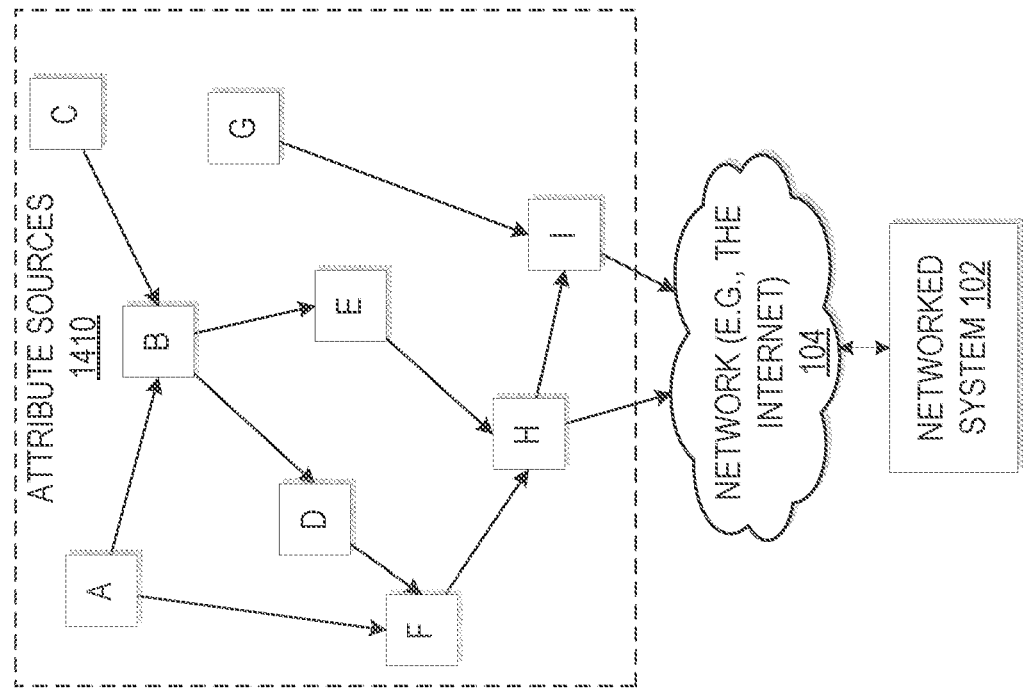

FIGS. 14A and 14B depict example configurations for communicatively coupling attribute sources, according to some example embodiments. The example embodiments described herein may access a vast and rich "Internet of Things" (IoT) dataset that is predominantly provided via communicatively connected, interconnected, or otherwise communicatively coupled machines and devices that may include a multitude of sensors. In example embodiments, devices and machines that provide the attribute data, such as the attribute sources, may be communicatively coupled in many different configurations. For instance, each attribute source may be communicatively coupled to the networked system 102 independently to provide the networked system 102 access to the attribute data corresponding to each of the communicatively coupled attribute sources. FIGS. 14A and 14B depict alternative example attribute source configurations. It will be appreciated that FIGS. 14A and 14B are merely non-limiting examples of attribute source configurations and many other configurations or suitable combinations of configurations may be employed.

FIG. 14A depicts an example embodiment that may include attribute sources 1410 communicatively coupled in a decentralized device-to-device mesh. In this example embodiment, the attribute data corresponding to a particular device in the mesh may be received from any one or more of the devices in the mesh. For instance, the networked system 102 may access the attribute data corresponding to attribute source E via attribute source H or a combination of attribute sources H and I in FIG. 14A. In an example embodiment, the attribute source H or I may aggregate and store the attribute data corresponding to attribute sources A-F in FIG. 14A. In some example embodiments, the networked system 102 may access the attribute data associated with attribute source E by communicating with attribute source H or I in FIG. 14A.

FIG. 14B depicts another example embodiment that may include attribute sources 1420 communicatively coupled to a central attribute source (e.g., attribute source H in FIG. 14B). The networked system 102 may access the attribute data associated with attribute sources A-G via the central attribute source in FIG. 14B. In some embodiments, the central attribute source may aggregate and store the attribute data received or accessed from the attribute sources A-G and provide a centralized access point for the attribute data associated with all, or some, of the communicatively coupled attribute sources A-G in FIG. 14B.

Figure 15:
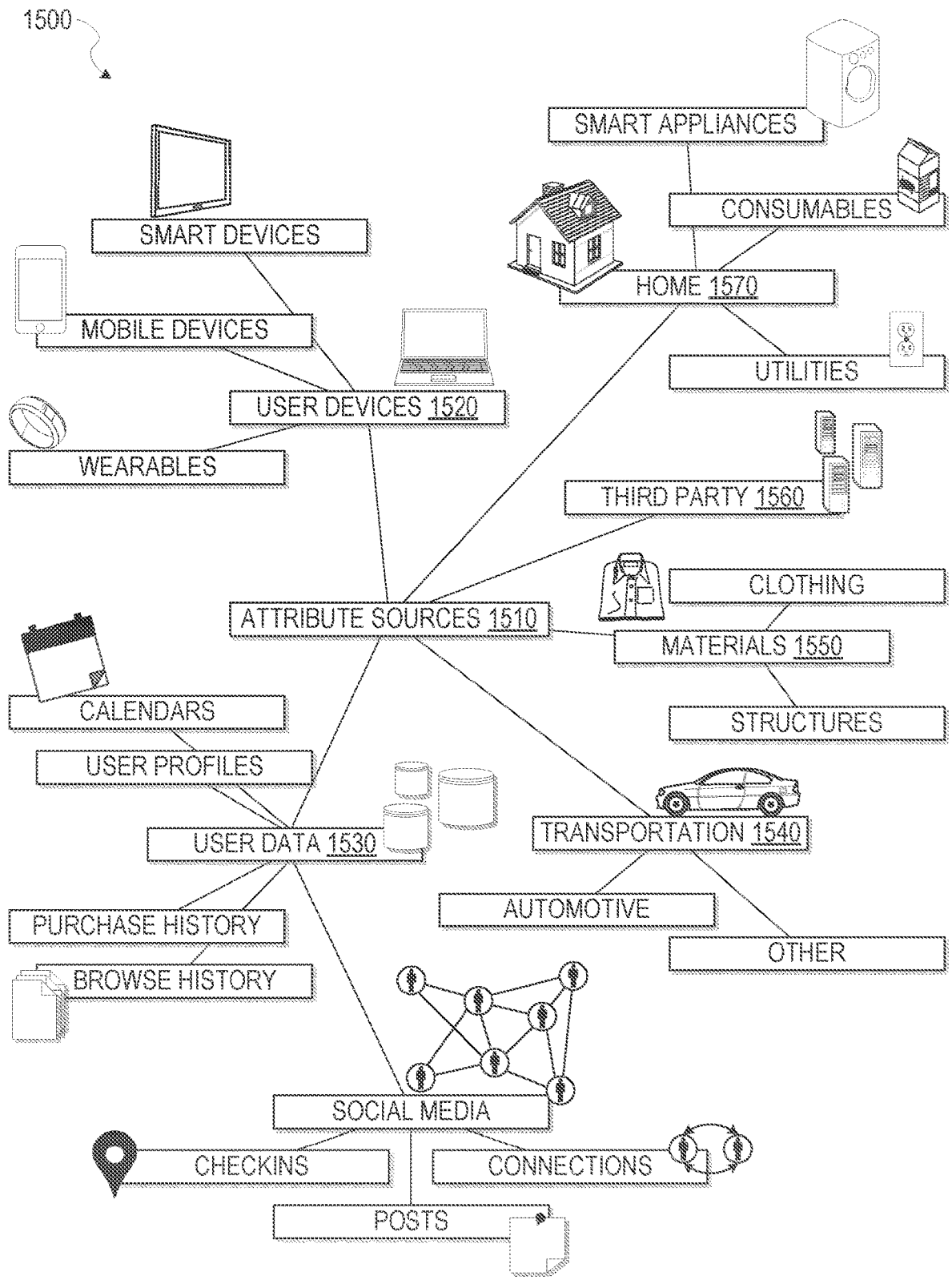
FIG. 15 depicts various example attribute sources, according to some example embodiments.

FIG. 15 depicts example sources 1500 including attribute sources 1510, according to some example embodiments. In various example embodiments, the attribute data may include data received, retrieved, or accessed from the attribute sources 1510. For example, the attribute sources 1510 may provide data including everything from a moisture level of a houseplant to a dribbling rhythm of a basketball. In some embodiments, the attribute data corresponding to the attribute sources 1510 may be received or accessed in real-time or near real-time. For instance, the attribute sources 1510 may communicate or otherwise provide access to the attribute data as it becomes available. In example embodiments, the attribute sources 1510 may include user device sources 1520, user data sources 1530, transportation sources 1540, materials sources 1550, third party sources 1560, home sources 1570, and a variety of other sources. As will be discussed in connection with FIG. 16 the attribute sources 1510 may be associated with a wide variety of sensors, gauges, measurement components, and other components.

In an example embodiment, the attribute data may include data corresponding to the user device sources 1520. The user device sources 1520 may include such non-limiting examples as a personal computer (PC), a tablet computer, a laptop computer, a netbook, a set-top box (STB), a personal digital assistant (PDA), an entertainment media system, a cellular telephone, a smart phone, a mobile device, a wearable device (e.g., a smart watch), a smart home device (e.g., a smart appliance), and other smart devices. As will be discussed further in connection with FIG. 16, the attribute data corresponding to the user device sources 1520 may include data associated with sensors, gauges, and other measurement components such as environmental sensor data (e.g., ambient temperature), biometric sensor data (e.g., heart rate), detection data (e.g., detection of a Near Field Communication (NFC) beacon), motion data (e.g., acceleration), position data (e.g., location as determined by a GPS of a mobile device), and so forth.

In further example embodiments, the attribute data corresponding to the user device sources 1520 may include data such as device type, device model, device name, a unique device identifier, and other device parameters. In some example embodiments, the device type data may provide a basis for an inference associated with the attribute data. For instance, if the device type data indicates that the device is a mobile device of the user, location data corresponding to the mobile device may indicate the location of the user. Similarly, if the device type is a media entertainment system, the attribute data corresponding to the media entertainment system may be associated with a home of the user.

The user data sources 1530 may include calendars (e.g., user calendar events such as birthdays, trips, exams), user profiles (e.g., demographic information such as age, gender, income level), purchase histories, browse histories (e.g., search terms), social media content (e.g., checkins, posts, connections), other user data (e.g., bookmarked websites, preferences or settings for various applications, application usage data such as time spent using a particular application), and the like. The attribute data corresponding to the user data sources 1530 may be stored, for example, by the user device sources 1520 (e.g., a mobile device that includes a mobile browser with browse history of the user), application server(s) 140 (e.g., payment history of the user stored in payment system(s) 144, user profiles stored by an e-commerce website), the third party server(s) 130 (e.g., social media data stored in a social networking service), and so on. For example, the attribute data corresponding to the user device sources 1520 may include device resource data. The device resource data may include files stored on the devices or metadata associated with the files. For instance, the device resources may include digital media files (e.g., MP3 formatted songs) or apps (e.g., pedometer app). The metadata associated with the device resources may include usage data such as number of times a song has been played, amount of time using a particular app, and so forth.

As cars and other forms of transportation become increasingly equipped with sensors and the ability to communicate, a vast amount of data may be provided by the transportation sources 1540. For example, the attribute data corresponding to the transportation sources 1540 may include acceleration data, velocity data, and other sensors data (e.g., brake pad wear data, gear shifting data). In this example, the attribute data corresponding to the transportation sources 1540 may provide indications of a user's driving patterns and styles (e.g., comes to a complete stop at a stop sign, speeds, or finicky use of the brakes).

The materials sources 1550, such as clothing and structures, are also increasingly gaining the ability to capture data. In various example embodiments, the attribute data may include data corresponding to the materials sources 1550. For example, clothing may be embedded with sensors to detect motion. Data from these sensors may provide indications of whether the user is agile or inactive. In another example, clothing may be embedded with biometric sensors that may provide continuous feed of biometric data corresponding to the user. The biometric data may provide indications of the user's health, athletic ability, and many other characteristics corresponding to the user. Similarly, structures may be equipped with sensors to passively or actively monitor the surrounding environment (e.g., street cameras, traffic cameras, and other sensors).

In example embodiments, the attribute data may include data associated with the third party sources 1560. The third party sources 1560 may also provide an abundance of data associated with the user. For instance, the attribute data may include data accessed from government websites or other public records that may provide criminal histories, civil citation histories, credit histories, or other publicly available information.

Nearly every facet of a smart home may be capable of providing data associated with the user. The attribute data may include data corresponding to the home sources 1570. For instance, the home sources 1570 may include smart appliances, consumables, utilities, and many other smart home devices. In a few specific instances, the attribute data may include consumable inventories and consumption rates of various consumable goods (e.g., milk, bread) tracked or monitored by smart refrigerators. In another instance, the attribute data may include utility usage data (e.g., electricity, water). Analysis of the utility usage data may indicate patterns or status of the user, such as, the user being on vacation, the user being ill (e.g., increasing house thermostat set temperature to cope with a cold), the user being an energy conscious consumer, and so on.

Figure 16:
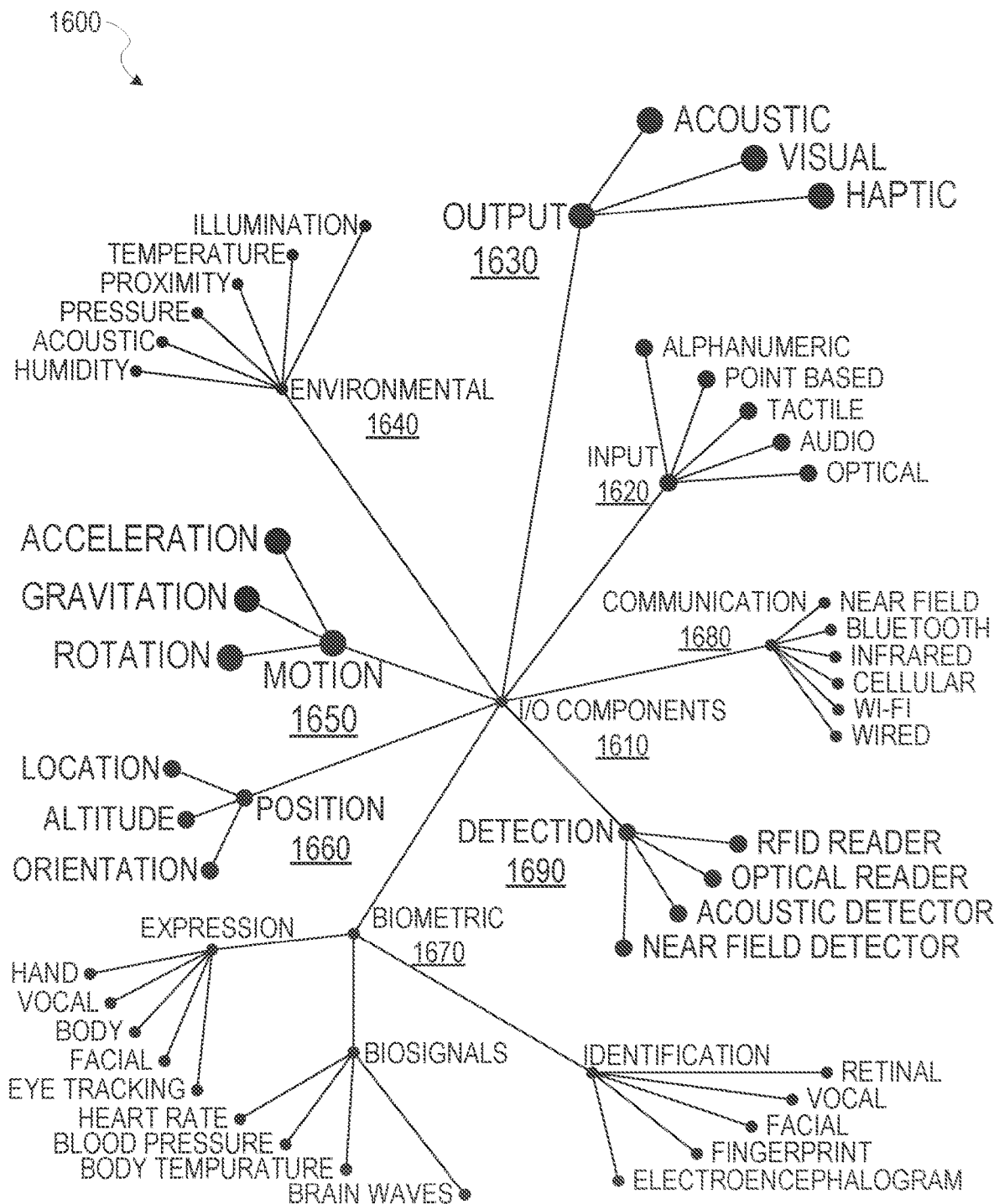
FIG. 16 depicts various components that provide attribute data, according to some example embodiments.

FIG. 16 depicts non-limiting example components 1600 that may provide attribute data according to some example embodiments. In example embodiments, I/O components 1610 may include input components 1620, output components 1630, environmental components 1640, motion components 1650, position components 1660, biometric components 1670, communication components 1680, detection components 1690, and a wide gamut of other sensors, gauges, and measurement components. The I/O components 1610 or a suitable combination of the I/O components 1610 may be included in any suitable device or machine such as those included in the attribute sources 1510 depicted in FIG. 15 to facilitate the functionality described herein. In various example embodiments, the attribute data provided by the I/O components 1610 may be accessible to all or some of the modules described above on a real-time or near real-time basis. The components 1600 are grouped according to functionality merely for simplifying the following discussion and the grouping is in no way limiting.

The input components 1620 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or other pointing instrument), tactile input components (e.g., a physical button, a touch screen that provide location and force of touches or touch gestures, or other tactile input components), audio input components (e.g., a microphone), and the like. The input components 1620 may receive input from the user to facilitate the functionalities described herein. For instance, the user may interact with a user interface using the input components 1620.

The output components 1630 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor), other signal generators, and so forth. The output components 1630 may present information to the user. For example, the output components 1630 may present a user interface to the user or present media files to the user.

The environmental components 1640 may include illumination sensors (e.g., photometer), temperature sensors (e.g., one or more thermometers that detect ambient temperature), humidity sensors, pressure sensors (e.g., barometer), acoustic sensors (e.g., one or more microphone that detects background noise), proximity sensors (e.g., an infrared sensor that detects nearby objects), gas sensors (e.g., gas detection sensors to detection concentrations of hazardous gases for safety or to measure pollutants in the atmosphere), and so on. The environmental components 1640 may measure various physical parameters to provide an indication or signal corresponding to the physical environment surrounding the environmental components 1640.

The motion components 1650 may include acceleration sensors (e.g., accelerometer), gravitation sensors, rotation sensors (e.g., gyroscope), and so forth. The motion components 1650 may provide motion data such as velocity, acceleration, or other force measurements along an x, y, and z axes. The motion data may be provided at a regular update rate (e.g., 10 updates per second) that may be configurable.

The position components 1660 may include location sensors (e.g., a Global Position System (GPS) receiver component), altitude sensors (e.g., altimeters or barometers that detect air pressure from which altitude may be derived), orientation sensors (e.g., magnetometers that provide magnetic field strength along the x, y, and z axes), and the like. In an example embodiment, the position components 1660 may provide position data such as latitude, longitude, altitude, and a time stamp. Similar to the motion components 1650, the position components 1660 may provide the motion data at a regular update rate that may be configurable.

The biometric components 1670 may include components to detect expressions, measure biosignals, or identify people, among other functions. For example, the biometric components 1670 may include expression components to detect expressions (also referred to as "kinesics") such as hand gestures (e.g., an optical component to detect a hand gesture or a Doppler component to detect hand motions), vocal expressions (e.g., a microphone to detect changes in voice pitch that may indicate tension), facial expressions (e.g., a camera to detect expressions or micro-expressions of a person such as a smile), body gestures, and eye tracking (e.g., detecting the focal point of a person's eyes or patterns in eye movement). The biometric components 1670 may also include, for example, biosignal components to measure biosignals such as blood pressure, heart rate, body temperature, perspiration, and brain waves (e.g., as determined by a electroencephalogram). In further examples, the biometric components 1670 may include identification components to identify people such as retinal scanners (e.g., a camera component), vocal detectors (e.g., a microphone to receive audio data for voice identification), facial detectors, fingerprint detectors, and electroencephalogram sensors (e.g., to identify a person via unique brain wave patterns).

Communication may be implemented using a wide variety of technologies. The I/O components 1610 may include communication components 1680 operable to communicatively couple machines or devices. For example, the communication components 1680 may include a network interface component or other suitable device to interface with a network (e.g., the network 104). In further examples, the communication components 1680 may include wired communication components, wireless communication components, cellular communication components, Near Field Communication (NFC) components, Bluetooth® components (e.g., Bluetooth® Low Energy), Wi-Fi® components, and other communication components to provide communication via other modalities. In addition, a variety of information may be derived using the communication components 1680 such as location via Internet Protocol (IP) geo-location, location via Wi-Fi® signal triangulation, location via detecting a NFC beacon signal that may indicate a particular location, and so forth.

The I/O components 1610 may include detection components 1690 that may detect a variety of identifiers. For example, the detection components 1690 may include Radio Frequency Identification (RFID) tag reader components, Near Field Communication (NFC) smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), and acoustic detection components (e.g., microphones to identify tagged audio signals).

Figure 17:
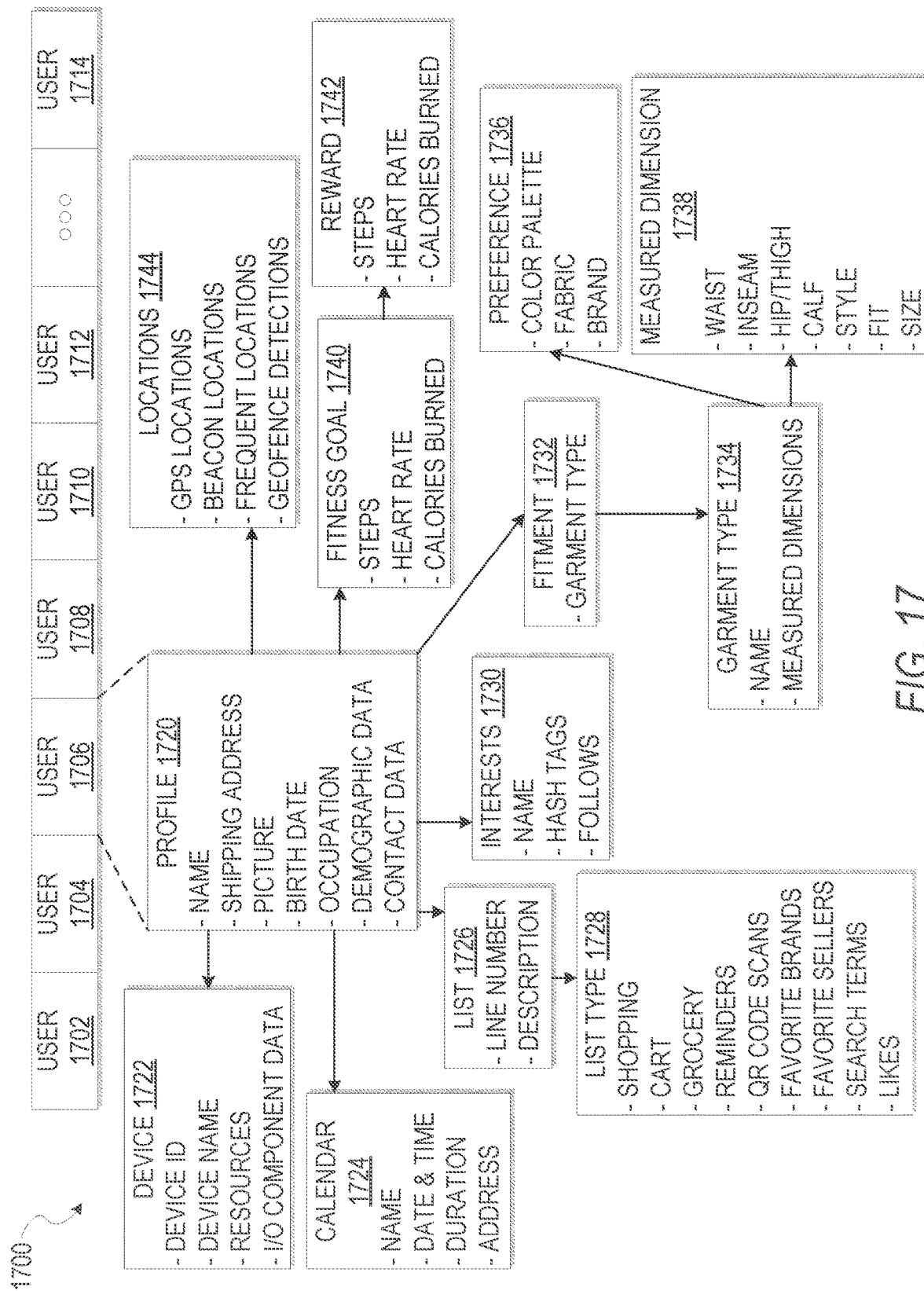
FIG. 17 is a block diagram of an example data structure for example attribute data associated with a user, according to some example embodiments.

FIG. 17 is a block diagram 1700 of an example data structure for the attribute data associated with a particular user according to example embodiments. In example embodiments, the attribute data may be associated with a plurality of users such as user 1702, 1704, 1706, 1708, 1710, 1712, and 1714. In an example embodiment, the attribute data may be accessed for a particular user by using a user identifier. The attribute data may include profile data 1720, device data 1722, calendar data 1724, list data 1726, list type data 1728, interest data 1730, fitment data 1732, garment type data 1734, preference data 1736, measured dimension data 1738, fitness goal data 1740, reward data 1742, location data 1744, and other data not shown. In some example embodiments, the attribute data may be structured such that various portions of the attribute data are associated with other portions of the attribute data via relationships. For instance, the calendar data 1724 may include a calendar event associated with an event name, an event data, and an event location for the calendar event.

FIG. 18 is a block diagram 1800 of an example data structure for data associated with a device according to some example embodiments. In an example embodiment, the device data 1722 of FIG. 17 may include a device identifier, a device name, device resources data (e.g., files stores on the devices such as browser cookies, media files), I/O component data, and so forth. In example embodiments, the device identifier may, for example, comprise an Internet Protocol (IP) address, a Media Access Control (MAC) address, other unique identifies, an International Mobile Station Equipment Identity (IMEI), or a Mobile Equipment Identifier (MEID). In an example embodiment, the I/O component data may include standard device parameters 1802, position data 1804, location data 1806, motion data 1808, environmental data 1810, biometric data 1812, and other data. FIG. 18 merely depicts example attribute data that may correspond to a particular device, and a variety of other data not shown may be included in the device data. The standard device parameters 1802 may include parameters that are standard across multiple devices included in the IoT. In various example embodiments, standardized parameters and protocols may facilitate access and utilization of the attribute data corresponding to such devices. For example, the attribute data available on an unknown device may be accessed and utilized without the need to discover or otherwise determine which parameters are available and which units of measure are associated with the parameters. Many other schemes may be employed to discover or otherwise determine available parameters accessible on a particular device.

Modules, Components, and Logic

Certain embodiments are described herein as including logic or a number of components, modules, or mechanisms. Modules may constitute either software modules (e.g., code embodied on a machine-readable medium or in a transmission signal) or hardware modules. A "hardware module" is a tangible unit capable of performing certain operations and may be configured or arranged in a certain physical manner. In various example embodiments, one or more computer systems (e.g., a standalone computer system, a client computer system, or a server computer system) or one or more hardware modules of a computer system (e.g., a processor or a group of processors) may be configured by software (e.g., an application or application portion) as a hardware module that operates to perform certain operations as described herein.

In some embodiments, a hardware module may be implemented mechanically, electronically, or any suitable combination thereof. For example, a hardware module may include dedicated circuitry or logic that is permanently configured to perform certain operations. For example, a hardware module may be a special-purpose processor, such as a Field-Programmable Gate Array (FPGA) or an Application Specific Integrated Circuit (ASIC). A hardware module may also include programmable logic or circuitry that is temporarily configured by software to perform certain operations. For example, a hardware module may include software encompassed within a general-purpose processor or other programmable processor. It will be appreciated that the decision to implement a hardware module mechanically, in dedicated and permanently configured circuitry, or in temporarily configured circuitry (e.g., configured by software) may be driven by cost and time considerations.

Accordingly, the phrase "hardware module" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented module" refers to a hardware module. Considering embodiments in which hardware modules are temporarily configured (e.g., programmed), each of the hardware modules need not be configured or instantiated at any one instance in time. For example, where a hardware module comprises a general-purpose processor configured by software to become a special-purpose processor, the general-purpose processor may be configured as respectively different special-purpose processors (e.g., comprising different hardware modules) at different times. Software may accordingly configure a particular processor or processors, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple hardware modules exist contemporaneously, communications may be achieved through signal transmission (e.g., over appropriate circuits and buses) between or among two or more of the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions described herein. As used herein, "processor-implemented module" refers to a hardware module implemented using one or more processors.

Similarly, the methods described herein may be at least partially processor-implemented, with a particular processor or processors being an example of hardware. For example, at least some of the operations of a method may be performed by one or more processors or processor-implemented modules. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an Application Program Interface (API)).

The performance of certain of the operations may be distributed among the processors, not only residing within a single machine, but deployed across a number of machines. In some example embodiments, the processors or processor-implemented modules may be located in a single geographic location (e.g., within a home environment, an office environment, or a server farm). In other example embodiments, the processors or processor-implemented modules may be distributed across a number of geographic locations.

Software Architecture

Figure 19:
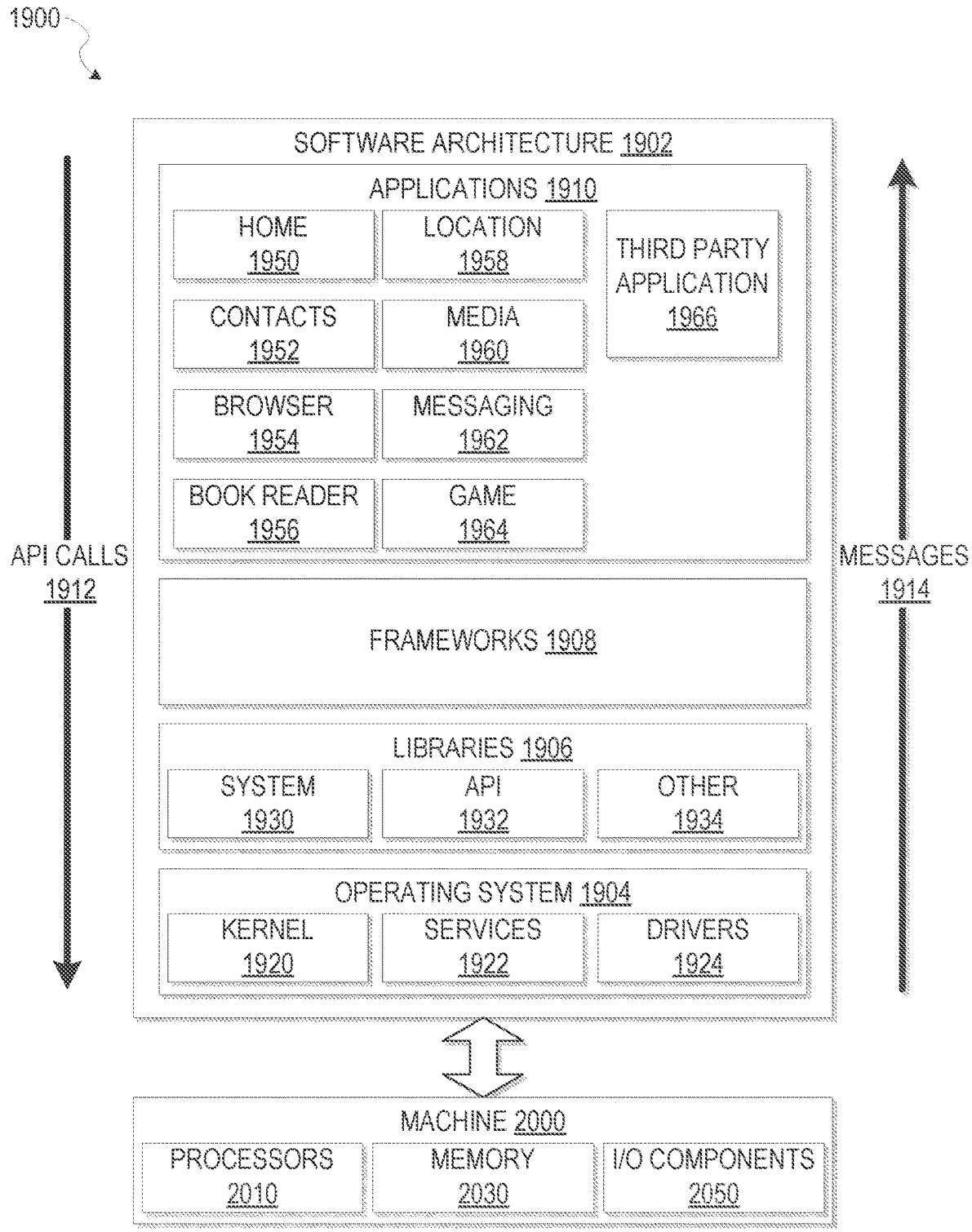
FIG. 19 is a block diagram illustrating an example of a software architecture that may be installed on a machine, according to some example embodiments.

FIG. 19 is a block diagram 1900 illustrating an architecture of software 1902, which may be installed on any one or more of devices described above. FIG. 19 is merely a non-limiting example of a software architecture and it will be appreciated that many other architectures may be implemented to facilitate the functionality described herein. The software 1902 may be executing on hardware such as machine 2000 of FIG. 20 that includes processors 2010, memory 2030, and I/O components 2050. In the example architecture of FIG. 19, the software 1902 may be conceptualized as a stack of layers where each layer may provide particular functionality. For example, the software 1902 may include layers such as an operating system 1904, libraries 1906, frameworks 1908, and applications 1910. Operationally, the applications 1910 may invoke application programming interface (API) calls 1912 through the software stack and receive messages 1914 in response to the API calls 1912.

The operating system 1904 may manage hardware resources and provide common services. The operating system 1904 may include, for example, a kernel 1920, services 1922, and drivers 1924. The kernel 1920 may act as an abstraction layer between the hardware and the other software layers. For example, the kernel 1920 may be responsible for memory management, processor management (e.g., scheduling), component management, networking, security settings, and so on. The services 1922 may provide other common services for the other software layers. The drivers 1924 may be responsible for controlling or interfacing with the underlying hardware. For instance, the drivers 1924 may include display drivers, camera drivers, Bluetooth® drivers, flash memory drivers, serial communication drivers (e.g., Universal Serial Bus (USB) drivers), Wi-Fi® drivers, audio drivers, power management drivers, and so forth.

The libraries 1906 may provide a low-level common infrastructure that may be utilized by the applications 1910. The libraries 1906 may include system 1930 libraries (e.g., C standard library) that may provide functions such as memory allocation functions, string manipulation functions, mathematic functions, and the like. In addition, the libraries 1906 may include API libraries 1932 such as media libraries (e.g., libraries to support presentation and manipulation of various media formats such as MPREG4, H.264, MP3, AAC, AMR, JPG, PNG), graphics libraries (e.g., an OpenGL framework that may be used to render 2D and 3D in a graphic content on a display), database libraries (e.g., SQLite that may provide various relational database functions), web libraries (e.g., WebKit that may provide web browsing functionality), and the like. The libraries 1906 may also include a wide variety of other libraries 1934 to provide many other APIs to the applications 1910.

The frameworks 1908 may provide a high-level common infrastructure that may be utilized by the applications 1910. For example, the frameworks 1908 may provide various graphic user interface (GUI) functions, high-level resource management, high-level location services, and so forth. The frameworks 1908 may provide a broad spectrum of other APIs that may be utilized by the applications 1910, some of which may be specific to a particular operating system or platform.

The applications 1910 include a home application 1950, a contacts application 1952, a browser application 1954, a book reader application 1956, a location application 1958, a media application 1960, a messaging application 1962, a game application 1964, and a broad assortment of other applications such as third party application 1966. In a specific example, the third party application 1966 (e.g., an application developed using the Android™ or iOS™ software development kit (SDK) by an entity other than the vendor of the particular platform) may be mobile software running on a mobile operating system such as iOS™, Android™ Windows® Phone, or other mobile operating systems. In this example, the third party application 1966 may invoke the API calls 1912 provided by the mobile operating system 1904 to facilitate functionality described herein.

Example Machine Architecture and Machine-Readable Medium

Figure 20:
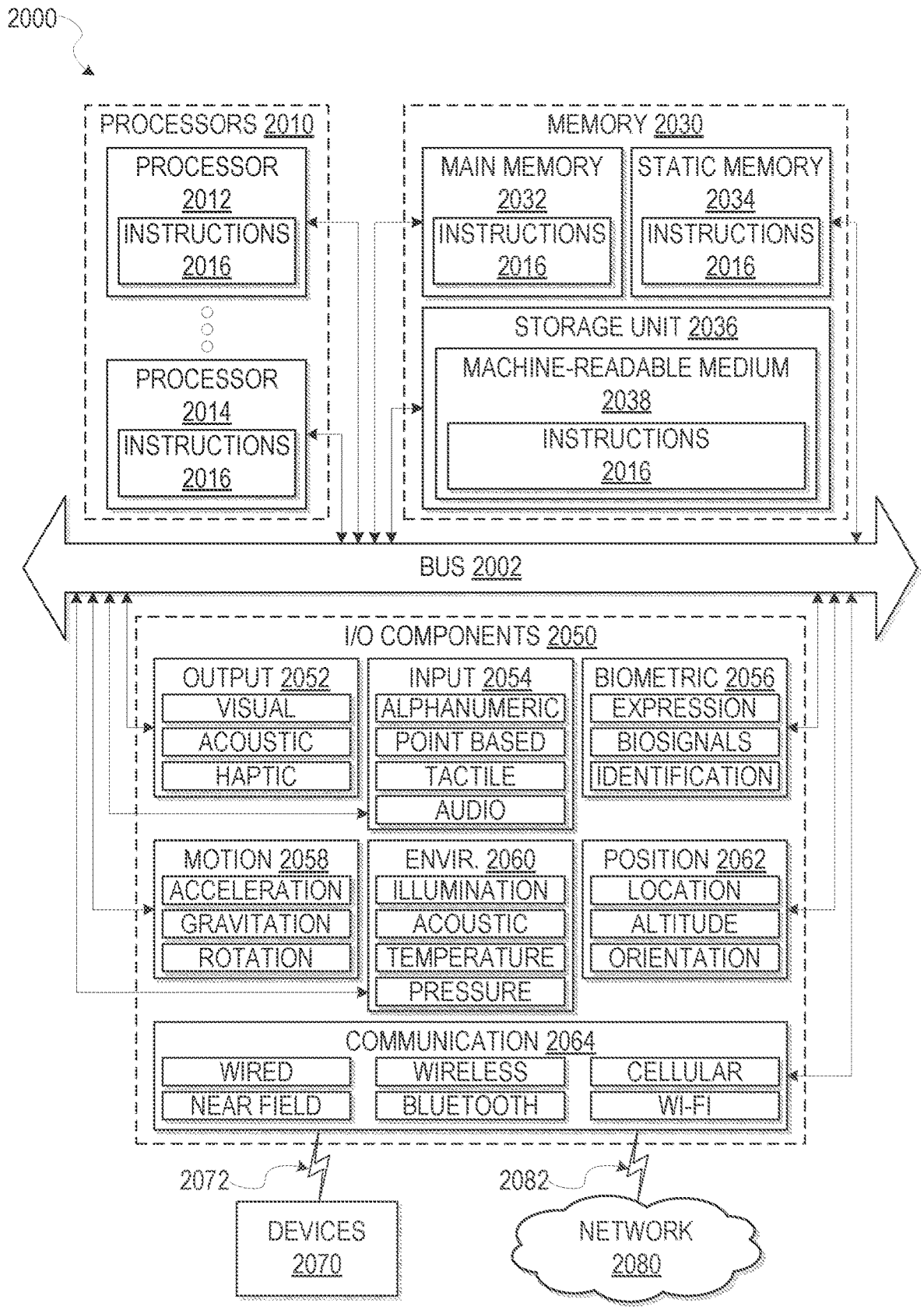
FIG. 20 illustrates a diagrammatic representation of a machine in the form of a computer system within which a set of instructions may be executed for causing the machine to perform any one or more of the methodologies discussed herein, according to an example embodiment.

FIG. 20 is a block diagram illustrating components of a machine 2000, according to some example embodiments, able to read instructions from a machine-readable medium (e.g., a machine-readable storage medium) and perform any one or more of the methodologies discussed herein. Specifically, FIG. 20 shows a diagrammatic representation of the machine 2000 in the example form of a computer system, within which instructions 2016 (e.g., software, a program, an application, an applet, an app, or other executable code) for causing the machine 2000 to perform any one or more of the methodologies discussed herein may be executed. In alternative embodiments, the machine 2000 operates as a standalone device or may be coupled (e.g., networked) to other machines. In a networked deployment, the machine 2000 may operate in the capacity of a server machine or a client machine in a server-client network environment, or as a peer machine in a peer-to-peer (or distributed) network environment. The machine 2000 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 2016, sequentially or otherwise, that specify actions to be taken by machine 2000. Further, while only a single machine 2000 is illustrated, the term "machine" shall also be taken to include a collection of machines 2000 that individually or jointly execute the instructions 2016 to perform any one or more of the methodologies discussed herein.

The machine 2000 may include processors 2010, memory 2030, and I/O components 2050, which may be configured to communicate with each other via a bus 2002. In an example embodiment, the processors 2010 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an Application Specific Integrated Circuit (ASIC), a Radio-Frequency Integrated Circuit (RFIC), another processor, or any suitable combination thereof) may include, for example, processor 2012 and processor 2014 that may execute instructions 2016. The term "processor" is intended to include multi-core processor that may comprise two or more independent processors (also referred to as "cores") that may execute instructions contemporaneously. Although FIG. 20 shows multiple processors, the machine 2000 may include a single processor with a single core, a single processor with multiple cores (e.g., a multi-core process), multiple processors with a single core, multiple processors with multiples cores, or any combination thereof.

The memory 2030 may include a main memory 2032, a static memory 2034, and a storage unit 2036 accessible to the processors 2010 via the bus 2002. The storage unit 2036 may include a machine-readable medium 2038 on which is stored the instructions 2016 embodying any one or more of the methodologies or functions described herein. The instructions 2016 may also reside, completely or at least partially, within the main memory 2032, within the static memory 2034, within at least one of the processors 2010 (e.g., within the processor's cache memory), or any suitable combination thereof, during execution thereof by the machine 2000. Accordingly, the main memory 2032, static memory 2034, and the processors 2010 may be considered as machine-readable media 2038.

As used herein, the term "memory" refers to a machine-readable medium 2038 able to store data temporarily or permanently and may be taken to include, but not be limited to, random-access memory (RAM), read-only memory (ROM), buffer memory, flash memory, and cache memory. While the machine-readable medium 2038 is shown in an example embodiment to be a single medium, the term "machine-readable medium" should be taken to include a single medium or multiple media (e.g., a centralized or distributed database, or associated caches and servers) able to store instructions 2016. The term "machine-readable medium" shall also be taken to include any medium, or combination of multiple media, that is capable of storing instructions (e.g., instructions 2016) for execution by a machine (e.g., machine 2000), such that the instructions, when executed by one or more processors of the machine 2000 (e.g., processors 2010), cause the machine 2000 to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" shall accordingly be taken to include, but not be limited to, one or more data repositories in the form of a solid-state memory (e.g., flash memory), an optical medium, a magnetic medium, other non-volatile memory (e.g., Erasable Programmable Read-Only Memory (EPROM)), or any suitable combination thereof. The term "machine-readable medium" specifically excludes non-statutory signals per se.

The I/O components 2050 may include a wide variety of components to receive input, provide output, produce output, transmit information, exchange information, capture measurements, and so on. It will be appreciated that the I/O components 2050 may include many other components that are not shown in FIG. 20. The I/O components 2050 are grouped according to functionality merely for simplifying the following discussion and the grouping is in no way limiting. In various example embodiments, the I/O components 2050 may include output components 2052 and input components 2054. The output components 2052 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor), other signal generators, and so forth. The input components 2054 may include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instrument), tactile input components (e.g., a physical button, a touch screen that provides location and force of touches or touch gestures, or other tactile input components), audio input components (e.g., a microphone), and the like.

In further example embodiments, the I/O components 2050 may include biometric components 2056, motion components 2058, environmental components 2060, or position components 2062 among a wide array of other components. For example, the biometric components 2056 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 2058 may include acceleration sensor components (e.g., accelerometer), gravitation sensor components, rotation sensor components (e.g., gyroscope), and so forth. The environmental components 2060 may include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 2062 may include location sensor components (e.g., a Global Position System (GPS) receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 2050 may include communication components 2064 operable to couple the machine 2000 to a network 2080 or devices 2070 via coupling 2082 and coupling 2072 respectively. For example, the communication components 2064 may include a network interface component or other suitable device to interface with the network 2080. In further examples, communication components 2064 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 2070 may be another machine or any of a wide variety of peripheral devices (e.g., a peripheral device coupled via a Universal Serial Bus (USB)).

Moreover, the communication components 2064 may detect identifiers or include components operable to detect identifiers. For example, the communication components 2064 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 2064, such as, location via Internet Protocol (IP) geo-location, location via Wi-Fi® signal triangulation, location via detecting a NFC beacon signal that may indicate a particular location, and so forth.

Transmission Medium

In various example embodiments, one or more portions of the network 2080 may be an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, the network 2080 or a portion of the network 2080 may include a wireless or cellular network and the coupling 2082 may be a Code Division Multiple Access (CDMA) connection, a Global System for Mobile communications (GSM) connection, or other type of cellular or wireless coupling. In this example, the coupling 2082 may implement any of a variety of types of data transfer technology, such as Single Carrier Radio Transmission Technology (1xRTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

The instructions 2016 may be transmitted or received over the network 2080 using a transmission medium via a network interface device (e.g., a network interface component included in the communication components 2064) and utilizing any one of a number of well-known transfer protocols (e.g., hypertext transfer protocol (HTTP)). Similarly, the instructions 2016 may be transmitted or received using a transmission medium via the coupling 2072 (e.g., a peer-to-peer coupling) to devices 2070. The term "transmission medium" shall be taken to include any intangible medium that is capable of storing, encoding, or carrying instructions 2016 for execution by the machine 2000, and includes digital or analog communications signals or other intangible medium to facilitate communication of such software.

Furthermore, the machine-readable medium 2038 is non-transitory (in other words, not having any transitory signals) in that it does not embody a propagating signal. However, labeling the machine-readable medium 2038 as "non-transitory" should not be construed to mean that the medium is incapable of movement; the medium should be considered as being transportable from one physical location to another. Additionally, since the machine-readable medium 2038 is tangible, the medium may be considered to be a machine-readable device.

Language

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the inventive subject matter has been described with reference to specific example embodiments, various modifications and changes may be made to these embodiments without departing from the broader scope of embodiments of the present disclosure. Such embodiments of the inventive subject matter may be referred to herein, individually or collectively, by the term "invention" merely for convenience and without intending to voluntarily limit the scope of this application to any single disclosure or inventive concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

As used herein, the term "or" may be construed in either an inclusive or exclusive sense. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

What is claimed is:

1. A method comprising:
    tracking, via one or more of a plurality of sources in an environment, activities of a user in the environment, the plurality of sources comprising one or more cameras that monitor the environment;
    determining, based on data from one or more of the plurality of sources in the environment, data associated with the user including inventory monitored by the one or more of the plurality of sources;
    receiving data from a device carried by the user, an identity of the user being derivable based on the data from the device; and
    augmenting one or more activities of the user based in part on the tracked activities and the data from the device, the augmenting the one or more activities including:
        facilitating a payment by the user, the facilitating the payment comprises causing the payment to be made based on the data from the device carried by the user; and
        providing a notification to the user regarding the payment.

2. The method of claim 1, wherein one or more of the plurality of sources further comprises an optical reader used to scan a code.

3. The method of claim 1, further comprising:
    equipping a structure with the one or more cameras to monitor the environment.

4. The method of claim 1, wherein facilitating the payment comprises causing the payment to be made without the user providing an additional security credential based on the data from the device carried by the user.

5. The method of claim 1, further comprising storing one or more user settings, wherein augmenting the one or more activities comprises:
    determining that a user setting of the one or more user settings is associated with an activity of the one or more activities; and
    augmenting the activity based on the user setting.

6. The method of claim 1, wherein tracking the activities comprises tracking inventories the user interacted with.

7. The method of claim 1, wherein providing the notification comprises causing presentation of the notification on the device carried by the user.

8. The method of claim 1, wherein the device comprises a commerce application.

9. A system comprising:
    one or more hardware processors; and
    a memory storing instructions that, when executed by the one or more hardware processors, causes the one or more hardware processors to perform operations comprising:
        tracking, via one or more of a plurality of sources in an environment, activities of a user in the environment;
        determining, based on data from one or more of the plurality of sources in the environment, data associated with the user including inventory monitored by one or more of the plurality of sources;

receiving data from a device carried by the user, an identity of the user being derivable based on the data from the device; and augmenting one or more activities of the user based in part on the tracked activities and the data from the device, the augmenting the one or more activities including:

facilitating a payment by the user, the facilitating the payment comprises causing the payment to be made without the user providing an additional security credential based on the data from the device carried by the user; and providing a notification to the user regarding the payment.

10. The system of claim 9, wherein one or more of the plurality of sources comprises an optical reader used to scan a code.

11. The system of claim 9, wherein one or more of the plurality of sources comprises one or more cameras that monitor the environment and track actions of the user.

12. The system of claim 9, wherein the operations further comprise equipping a structure with cameras to monitor the environment.

13. The system of claim 9, wherein the operations further comprise storing one or more user settings, wherein augmenting the one or more activities comprises:

determining that a user setting of the one or more user settings is associated with an activity of the one or more activities; and augmenting the activity based on the user setting.

14. The system of claim 9, wherein tracking the activities comprises tracking inventories the user interacted with.

15. The system of claim 9, wherein providing the notification comprises causing presentation of the notification on the device carried by the user.

16. The system of claim 9, wherein the device comprises a commerce application.

17. A non-transitory machine-storage medium storing instructions that, when executed by one or more hardware processors of a machine, cause the machine to perform operations comprising:

tracking, via one or more of a plurality of sources in an environment, activities of a user in the environment, the plurality of sources comprising one or more cameras that monitor the environment;

determining, based on data from one or more of the plurality of sources in the environment, data associated with the user including inventory monitored by one or more of the plurality of sources;

receiving data from a device carried by the user, an identity of the user being derivable based on the data from the device; and augmenting one or more activities of the user based in part on the tracked activities and the data from the device, the augmenting the one or more activities including:

facilitating a payment by the user, wherein facilitating the payment comprises causing the payment to be made based on the data from the device carried by the user; and providing a notification to the user regarding the payment.

* * * * *